United States Patent
Kim et al.

(10) Patent No.: US 11,506,613 B2
(45) Date of Patent: Nov. 22, 2022

(54) FLUID ANALYSIS APPARATUS AND METHOD OF CONTROLLING THE SAME

(71) Applicant: PRECISION BIOSENSOR INC., Daejeon (KR)

(72) Inventors: Hong-Geun Kim, Suwon-si (KR); Hyun-Suk Kang, Suwon-si (KR); Jong Gun Lee, Yongin-si (KR); Jong Cheol Kim, Seoul (KR); Seung Woo Han, Busan (KR)

(73) Assignee: PRECISION BIOSENSOR INC., Daejeon (KR)

( * ) Notice: Subject to any disclaimer, the term of this patent is extended or adjusted under 35 U.S.C. 154(b) by 91 days.

(21) Appl. No.: 16/968,484

(22) PCT Filed: Oct. 2, 2018

(86) PCT No.: PCT/KR2018/011706
§ 371 (c)(1),
(2) Date: Aug. 7, 2020

(87) PCT Pub. No.: WO2019/156306
PCT Pub. Date: Aug. 15, 2019

(65) Prior Publication Data
US 2020/0400582 A1    Dec. 24, 2020

(30) Foreign Application Priority Data
Feb. 8, 2018    (KR) .................. 10-2018-0015486

(51) Int. Cl.
*G01N 21/59*    (2006.01)
*G01N 21/77*    (2006.01)
(Continued)

(52) U.S. Cl.
CPC ............. *G01N 21/77* (2013.01); *G01N 21/85* (2013.01); *G01N 21/27* (2013.01); *G01N 33/487* (2013.01)

(58) Field of Classification Search
CPC ........ A61B 5/15003; A01H 1/02; A01H 5/10; G01N 21/77; G01N 21/27; G01N 21/85;
(Continued)

(56) References Cited

U.S. PATENT DOCUMENTS 7,983,391 B2    7/2011   Machan et al.
8,089,053 B1    1/2012   Finch
(Continued)

FOREIGN PATENT DOCUMENTS

EP    0 341 829 B1    8/1994
JP    2005-221435 A    8/2005
(Continued)

OTHER PUBLICATIONS

International Search Report dated Jan. 25, 2019 issued by the International Searching Authority in counterpart International Application No. PCT/KR2018/011706 (PCT/ISA/210).
(Continued)

*Primary Examiner* — Hoa Q Pham
(74) *Attorney, Agent, or Firm* — Lex IP Meister, PLLC

(57) ABSTRACT

Provided is a fluid analysis apparatus and a method of controlling the same. The fluid analysis apparatus include an actuator provided on a part of the fluid analysis apparatus, a mounting portion on which a fluid accommodating cartridge is mounted thereon, the fluid accommodating cartridge provided with a well in which a fluid sample is accommodated, a measurement portion configured to transmit light to the fluid accommodating cartridge and detect an optical signal from the light passed through the fluid accommodating cartridge, and a controller configured to control an
(Continued)

operation of the actuator based on the optical signal detected by the measurement portion such that the light transmitted from the measurement portion passes through a central portion of the well to perform an accurate inspection on the fluid sample.

10 Claims, 26 Drawing Sheets

(51) Int. Cl.
    *G01N 21/85*     (2006.01)
    *G01N 21/27*     (2006.01)
    *G01N 33/487*     (2006.01)

(58) Field of Classification Search
    CPC .. G01N 21/59; G01N 21/13; G01N 2201/061; G01N 2201/0256
    USPC ............. 356/39–41, 432–440, 246; 422/100; 250/206, 559.3
    See application file for complete search history.

(56) References Cited

U.S. PATENT DOCUMENTS

| | | | |
|---|---|---|---|
| 9,869,631 B2* | 1/2018 | Jo | G01N 21/13 |
| 2003/0146282 A1 | 8/2003 | Tsikos et al. | |
| 2006/0256336 A1* | 11/2006 | Fritz | G01B 11/272 356/399 |
| 2010/0137778 A1 | 6/2010 | Kunjan et al. | |
| 2012/0215095 A1 | 8/2012 | Av-Shalom et al. | |
| 2013/0119277 A1* | 5/2013 | Atzler | G01J 3/0291 250/206 |
| 2015/0132860 A1* | 5/2015 | Cook | B01L 3/502715 436/501 |
| 2018/0064384 A1* | 3/2018 | Galen | G01N 1/312 |

FOREIGN PATENT DOCUMENTS

| | | |
|---|---|---|
| JP | 2008-116441 A | 5/2008 |
| KR | 10-2011-0091309 A | 8/2011 |
| KR | 10-2015-0074624 A | 7/2015 |
| KR | 10-2015-0090747 A | 8/2015 |
| KR | 10-2017-0082206 A | 7/2017 |

OTHER PUBLICATIONS

Communication dated Apr. 6, 2022 issued by the Korean Intellectual Property Office in Korean Application No. 10-2018-0015486.

* cited by examiner

1

1

(a)

(b)

(c)

(a)

(b)

(c)

(a)

(b)           (c)

(a)

(b)

(c)

(a)

(b)

(c)

(a)

(b)         (c)

(a)

(b)

(c)

FLUID ANALYSIS APPARATUS AND METHOD OF CONTROLLING THE SAME

TECHNICAL FIELD

The disclosure relates to a fluid analysis apparatus for inspecting and analyzing a fluid sample, such as blood, and a method of controlling the same.

BACKGROUND ART

In general, a fluid analysis apparatus for inspecting and analyzing a fluid sample is used while accommodating a fluid sample in a fluid accommodating cartridge. For example, a fluid analysis apparatus, such as an in vitro diagnostic tester, employs a fluid accommodating cartridge into which a fluid sample containing biological information, such as genes, is injected. The fluid accommodating cartridge includes a fluid supply portion and a well in which a reagent is accommodated. When the fluid accommodating cartridge is mounted on the fluid analysis apparatus for inspection, the fluid sample is caused to move to the well containing the reagent and reacts with the reagent. The fluid analysis apparatus derives a component of the fluid sample based on an optical signal resulting from detecting light passing through a fluid reactant.

In this regard, the accuracy in mounting the fluid accommodating cartridge at the correct position of the fluid analysis apparatus is significantly important. The conventional technology is equipped with a sensor to determine whether the fluid accommodating cartridge is installed, but has a limitation in accurately recognizing the mounting of the fluid accommodating cartridge, and sometimes resulted in incorrect inspection results.

In addition, even after recognizing that the fluid accommodating cartridge is incorrectly mounted, it is difficult for a user to accurately mount the fluid accommodating cartridge by finely moving the fluid accommodating cartridge, so that the user may attempt to manually re-install the fluid analysis apparatus several times. In particular, when a plurality of fluid accommodating cartridges are mounted for various inspections, the user may have considerable inconvenience.

DISCLOSURE

Technical Problem

One aspect of the disclosure provides an apparatus and a method that are capable of determining a mounting state of a fluid accommodating cartridge for inspecting and analyzing a fluid sample contained in a fluid accommodating cartridge, and upon the fluid accommodating cartridge being correctly mounted, performing a corrective action.

Technical Solution

According to an aspect of the disclosure, there is provided a fluid analysis apparatus including: an actuator provided on a part of the fluid analysis apparatus; a mounting portion on which a fluid accommodating cartridge is mounted thereon, the fluid accommodating cartridge provided with a well in which a fluid sample is accommodated; a measurement portion configured to transmit light to the fluid accommodating cartridge and detect an optical signal from the light passed through the fluid accommodating cartridge; and a controller configured to control an operation of the actuator based on the optical signal detected by the measurement portion such that the light transmitted from the measurement portion passes through a central portion of the well to perform an accurate inspection on the fluid sample.

The controller may control the operation of the actuator to align the measurement portion with the well such that the light transmitted from the measurement portion passes through the central portion of the well.

The measurement portion may include: a light source portion configured to transmit light to the well of the fluid accommodating cartridge; and a light detection portion configured to detect optical signals from the transmitted light, wherein the controller may control the operation of the actuator such that a center of the light source portion, a center of the light detection portion, and a center of the well are vertically in line with each other within an error range of a predetermined diameter.

The actuator may be provided on the mounting portion or the measurement portion, and the controller may control the operation of the actuator to move the mounting portion or the measurement portion such that the light transmitted from the measurement portion passes through the central portion of the well.

The controller may control the operation of the actuator to move a pin hole portion included in the measurement portion.

The controller may control the operation of the actuator based on a width of the optical signal.

The controller may be configured to: identify that the fluid accommodating cartridge is abnormally mounted when the width of the optical signal falls outside of an allowable range, and control the operation of the actuator such that the width of the optical signal falls within the allowable range.

The controller may be configured to: upon identifying that the fluid accommodating cartridge is abnormally mounted, identify a mis-installation direction of the fluid accommodating cartridge by controlling the operation of the actuator, and control the operation of the actuator such that the width of the optical signal falls within the allowable range based on the mis-installation direction.

The controller may control the operation of the actuator based on a strength of the optical signal.

The controller may be configured to: identify that the fluid accommodating cartridge is abnormally mounted when the strength of the optical signal falls outside of an allowable range, and control the operation of the actuator such that the strength of the optical signal falls within the allowable range.

The controller may be configured to: upon identifying that the fluid accommodating cartridge is abnormally mounted, identify a mis-installation direction of the fluid accommodating cartridge by controlling the operation of the actuator, and control the operation of the actuator such that the strength of the optical signal falls within the allowable range based on the mis-installation direction.

The measurement portion may transmit the light to at least one of the well or a groove provided in the fluid accommodating cartridge, and detect the optical signal from the light passed through the at least one of the well or the groove.

When a plurality of the actuators may be mounted on the mounting portion, the controller may move the mounting portion in an upward direction, a downward direction, a clockwise direction, or a counter-clockwise direction by controlling the plurality of actuators.

According to another aspect of the disclosure, there is provided a method of controlling a fluid analysis apparatus, the method including: transmitting light to a fluid accommodating cartridge provided with a well in which a fluid sample is accommodated; detecting an optical signal from the light passed through the fluid accommodating cartridge; and controlling an operation of an actuator based on the detected optical signal such that the light transmitted to the fluid accommodating cartridge passes through a central portion of the well to perform an accurate inspection on the fluid sample.

The controlling of the actuator may include controlling the operation of the actuator to align a measurement portion configured to transmit the light with the well such that the light passes through the central portion of the well.

The controlling of the actuator to align the measurement portion with the well may include controlling the operation of the actuator such that a center of a light source portion configured to transmit light to the well, a center of a light detection portion configured to detect optical signals from the transmitted light, and a center of the well are vertically in line with each other within an error range of a predetermined diameter.

The controlling of the actuator may include controlling the operation of the actuator based on a width of the optical signal.

The controlling of the actuator may include: identifying that the fluid accommodating cartridge is abnormally mounted when the width of the optical signal falls outside of an allowable range; and controlling the operation of the actuator such that the width of the optical signal falls within the allowable range.

The controlling of the actuator may include controlling the operation of the actuator based on a strength of the optical signal.

The controlling of the actuator may include: identifying that the fluid accommodating cartridge is abnormally mounted when the strength of the optical signal falls outside of an allowable range; and controlling the operation of the actuator such that the strength of the optical signal falls within the allowable range.

Advantageous Effects

As is apparent from the above, the fluid analysis apparatus can finely align a light source portion for transmitting light to a well with a light detection portion for receiving light passed through the well by controlling an operation of an actuator. Accordingly, the performance of the fluid analysis apparatus is improved, and a fluid sample accommodated in the well of the fluid accommodating cartridge is accurately analyzed, so that the productivity for analyzing the fluid sample can be increased.

In addition, the inconvenience of a user using the fluid analysis apparatus is reduced by an automatic alignment operation of the fluid analysis apparatus, so that the user satisfaction can be improved.

MODES OF THE DISCLOSURE

Hereinafter, preferred embodiments of the disclosure will be described in detail with reference to the accompanying drawings.

On the other hand, the terms "front end", "rear end", "upper part", "lower part", "upper end" and "lower end" used in the following description are defined based on the drawings, and the shape and position of each component is not limited by these terms. In addition, in the disclosure, a fluid sample refers to a substance to be inspected and analyzed by a fluid analysis apparatus, and represent an object to be measured, a fluid sample, or a specimen. The fluid sample may include bio-samples, such as body fluids, blood, tissue fluids, and lymph fluids, saliva, urine, and the like, or environmental samples for water quality management or soil management, but the disclosure is not limited thereto.

Figure 1:
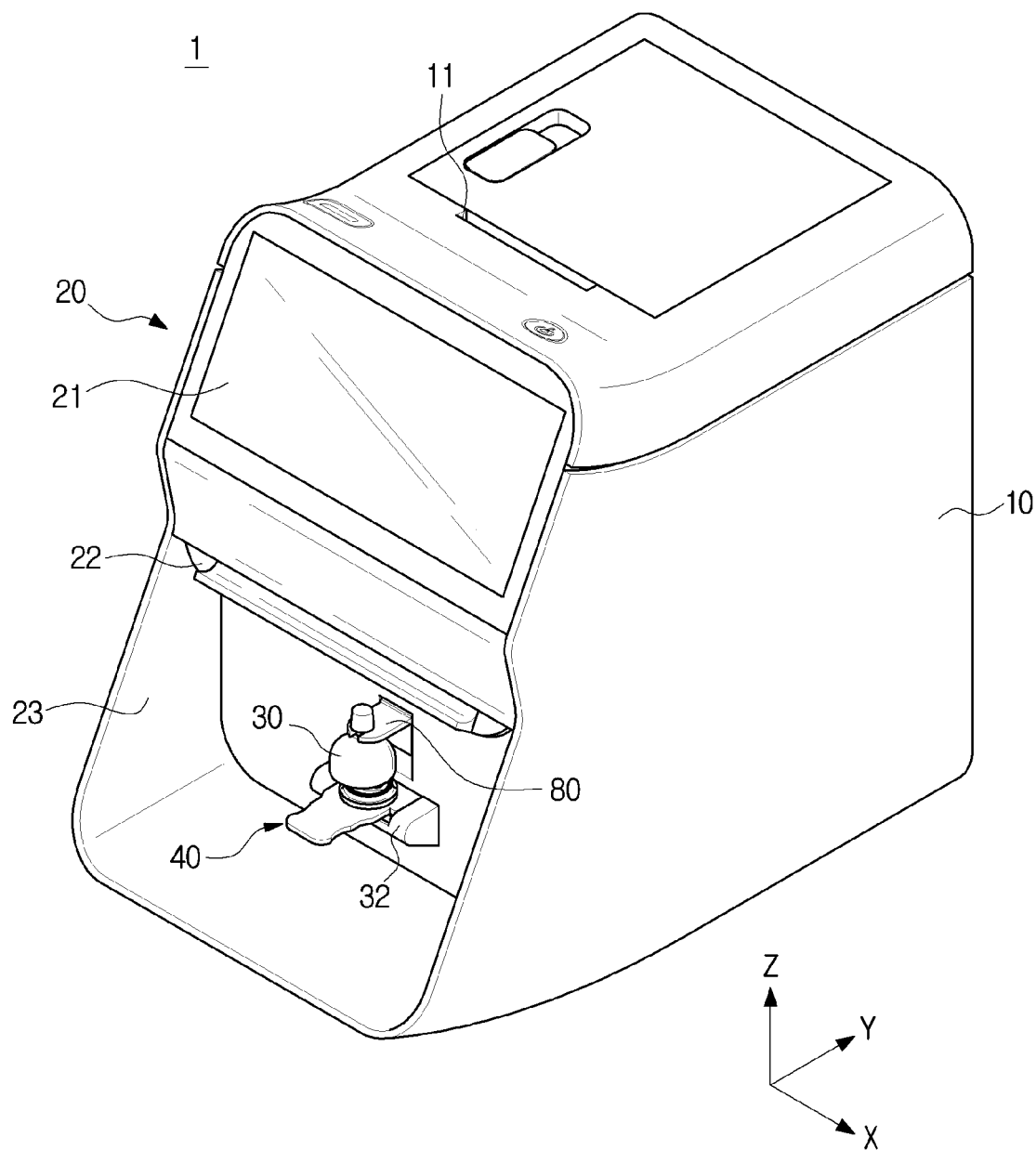
FIG. 1 is a view illustrating a fluid analysis apparatus equipped with a fluid accommodating cartridge according to an embodiment of the disclosure.

FIG. 1 is a view illustrating a fluid analysis apparatus equipped with a fluid accommodating cartridge according to an embodiment of the disclosure.

Referring to FIG. 1, a fluid analysis apparatus 1 to which a fluid accommodating cartridge 40 according to an embodiment of the disclosure is coupled includes a housing 10 forming the external appearance thereof and a door module 20 provided on the front of the housing 10.

The door module 20 may include a display 21, a door 22, and a door frame 23. The display 21 and the door 22 may be disposed on the front of the door frame 23. The display 21 may be located above the door 22. The door 22 may be slidably provided such that the door 22 sliding to open may be located behind the display 21.

The display 21 may display information regarding a fluid sample analysis content, a fluid sample analysis operation state, and the like. The door frame 23 may be provided with a mounting portion 32 on which the fluid accommodating cartridge 40 may be mounted. A user may open the door 22 by sliding the door 40 upward, mount the fluid accommodating cartridge 40 on the mounting portion 32, closes the door 22 by sliding the door 22 downward, and perform an analysis operation.

The fluid analysis apparatus 1 may further include a fluid accommodating cartridge 40. The fluid accommodating cartridge 40 may be provided with wells containing fluid samples. The fluid accommodating cartridge 40 may be detachably coupled to the fluid analysis apparatus 10.

Figure 2A:
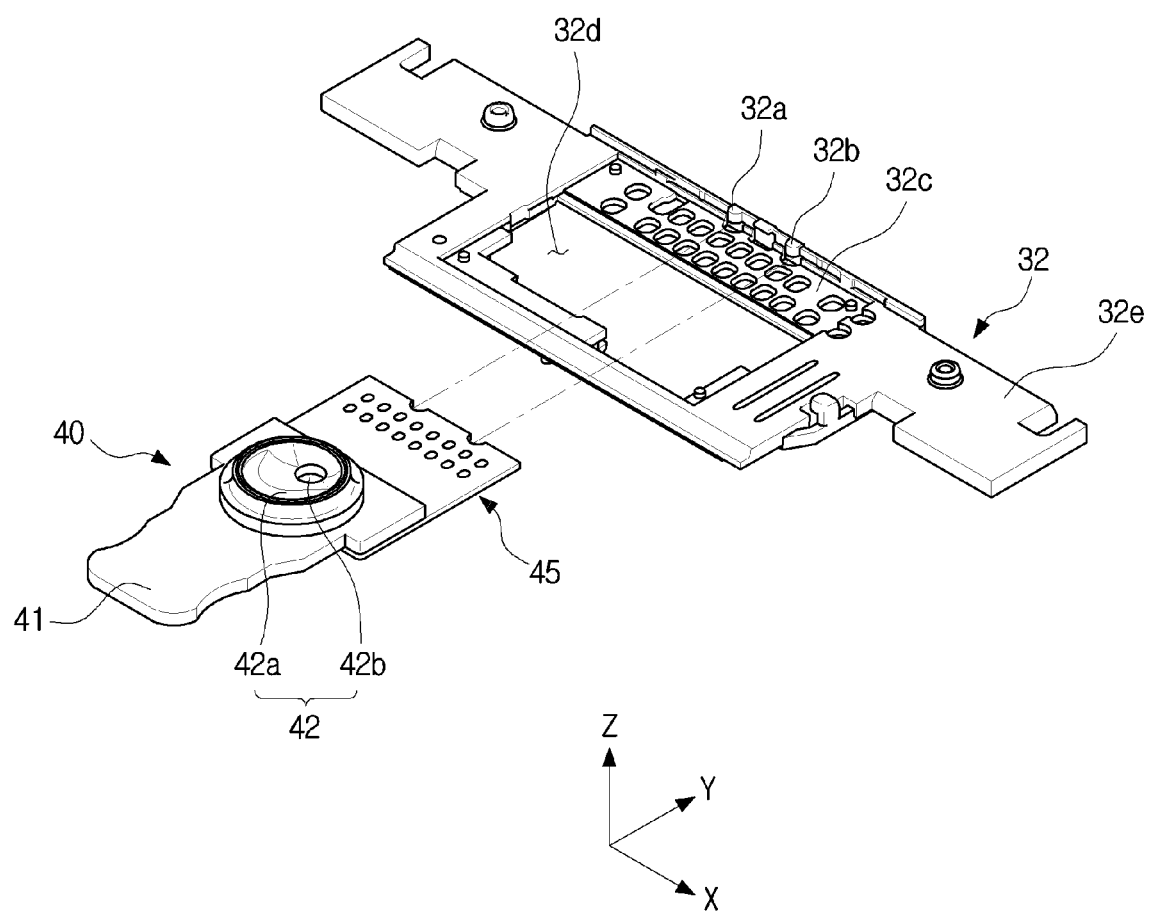
FIG. 2A is a perspective view illustrating according to an embodiment of the disclosure, showing a state in which a fluid accommodating cartridge is separated from a mounting portion.

A fluid sample may be injected into the fluid accommodating cartridge 40, and have a reaction with a reagent in an inspection unit (45 in FIG. 2A). The fluid accommodating cartridge 40 is inserted into the mounting portion 32, and a pressing portion 30 presses the fluid accommodating cartridge 40 so that the fluid sample in the fluid accommodating cartridge 40 is introduced into the inspection unit (45 in FIG. 2A). The pressing portion 30 may be coupled to a lever 80 of the fluid analysis apparatus 1.

The fluid analysis apparatus 1 may further include an output portion 11 provided separately from the display 21 to output inspection results as separate printed material.

The fluid analysis apparatus 1 may further include the pressing portion 30. The pressing portion 30 serves to compress a fluid sample to move the fluid sample to the inspection unit 45. In other words, the pressing portion 30 serves to apply a pressure to a fluid sample such that the fluid sample is moved to the inspection unit (45 in FIG. 2A).

The pressing portion 30 may be arranged to press the fluid accommodating cartridge 40. Specifically, the pressing portion 30 may be arranged to press a fluid supply portion (42 of FIG. 2A). The pressing portion 30 may be arranged to press the fluid supply portion (42 of FIG. 2A) such that a fluid sample supplied to the fluid supply unit (42 of FIG. 2A) is moved to the inspection unit (45 of FIG. 2A). The pressing portion 30 may press the fluid supply portion (42 in FIG. 2A) by moving in the vertical direction. In other words, the pressing portion 30 may press the fluid supply portion (42 in FIG. 2A) using the lever principle. The pressing portion 30 may be coupled to the lever 80. The lever 80 is coupled to a shaft (not shown) provided inside the fluid analysis apparatus 1 so as to be movable in the vertical direction. Therefore, the pressing portion 30 coupled to the lever 80 may move in the vertical direction together with the lever 80.

The pressing portion 30 may be formed of at least one of an elastic material or a ductile material. As an example, the pressing portion 30 may be formed of a rubber material.

Figure 2B:
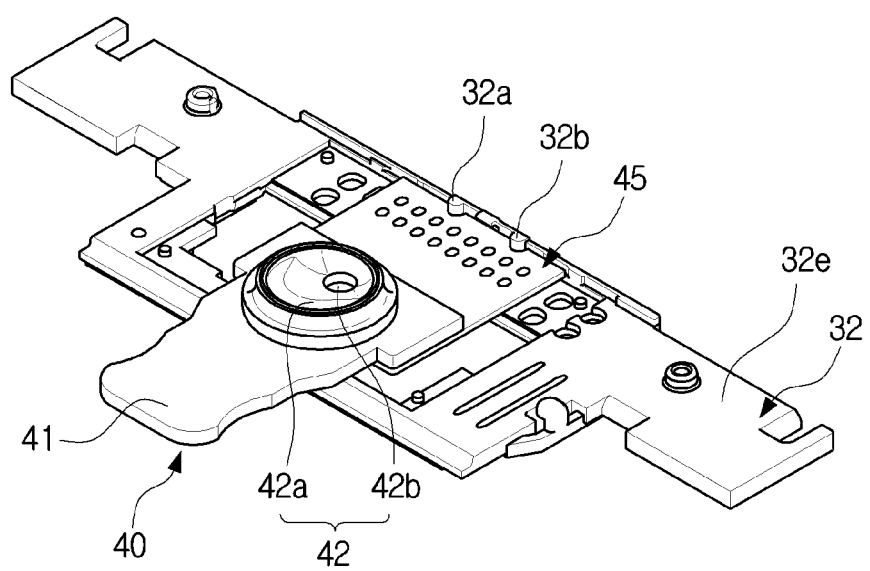
FIG. 2B is a perspective view illustrating according to an embodiment of the disclosure, showing a state in which a fluid accommodating cartridge is coupled to a mounting portion.
Figure 3:
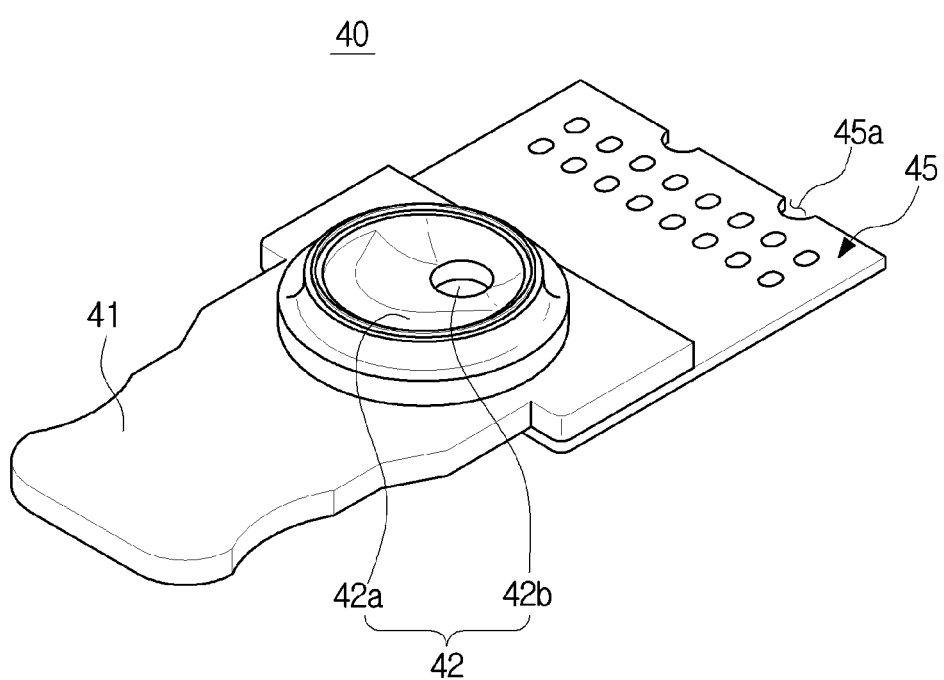
FIG. 3 is a perspective view illustrating a fluid accommodating cartridge according to an embodiment of the disclosure.

FIG. 2A is a perspective view illustrating according to an embodiment of the disclosure, showing a state in which a fluid accommodating cartridge is separated from a mounting portion, FIG. 2B is a perspective view illustrating according to an embodiment of the disclosure, showing a state in which a fluid accommodating cartridge is coupled to a mounting portion, and FIG. 3 is a perspective view illustrating a fluid accommodating cartridge according to an embodiment of the disclosure.

Figure 2B:
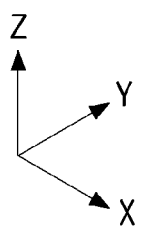

Referring to FIGS. 2A to 3, the fluid accommodating cartridge 40 may be inserted into the mounting portion 32 of the fluid analysis apparatus 1. A seating portion 32c may be provided in the center of a body 32e of the mounting portion 32. A slit 32d may be provided at the rear of the seating portion 32c. The slit 32d is provided to prevent an error that may occur when measuring the inspection result of the fluid sample of the inspection unit 45.

The mounting portion 32 includes contact portions 32a and 32b that make contact with the fluid accommodating cartridge 40, and the inspection unit 45 of the fluid accommodating cartridge 40 may include depression portions 45a having a shape corresponding to those of the contact portions 32a and 32b. The depression portions 45a may come into contact with the contact portions 32a and 32b. The depression portions 45a and the contact portions 32a and 32b may each be provided as two units thereof, but the number of the depression portions 45a and the contact portions 32a and 32b is not limited thereto.

The fluid accommodating cartridge 40 may include a housing 41 forming the external appearance thereof and the inspection unit 45 in which a reaction occurs as a fluid sample meets a reagent.

The housing 41 may support the fluid accommodating cartridge 40. In addition, the housing 41 may include a gripping portion that allows a user to grip the fluid accommodating cartridge 40. The gripping portion is formed in a streamlined projection shape so that the user may stably grip the fluid accommodating cartridge 40.

In addition, the fluid accommodating cartridge 40 may be provided with the fluid supply portion 42 for supplying a fluid sample. Specifically, the fluid supply portion 42 may be provided in the housing 41. The fluid supply portion 42 may include a supply hole 42b through which a fluid sample flows into the inspection unit 45 and a supply auxiliary portion 42a to assist the supply of the fluid sample. The fluid supply portion 42 may be supplied with a fluid sample that is to be inspected by the fluid analysis apparatus 1.

The supply hole 42b may be formed in a circular shape, but the shape of the supply hole 42b is not limited thereto, and may be formed in a polygonal shape. A user may drop a fluid sample into the fluid supply portion 42 using a tool, such as a pipet or a dropper. The supply auxiliary portion 42a may be formed at a circumference of the supply hole 42b to be inclined toward the supply hole 42b. Accordingly, the fluid sample dropped around the supply hole 42b may flow into the supply hole 42b along the slope. Specifically, when a user fails to drop a fluid sample accurately into the supply hole 42b and a part of the fluid sample is dropped around the supply hole 42b, the fluid sample dropped around the supply hole 42b may be caused to flow into the supply hole 42b by the slope of the supply auxiliary part 42a.

In addition, the supply auxiliary portion 42a does not only assist in supplying the fluid sample, but also prevents the fluid accommodating cartridge 40 from being contaminated by the incorrectly supplied fluid sample. Specifically, even when a fluid sample does not exactly flow into the supply hole 42b, the supply auxiliary portion 42a formed at a circumference of the supply hole 42b prevents the fluid sample from flowing toward the inspection unit 45 or the gripping portion, thereby preventing the fluid sample from contaminating the fluid accommodating cartridge 40. In addition, the supply auxiliary portion 42a may prevent a fluid sample that may be harmful to the human body from coming into contact with the user.

The fluid supply portion 42 may include at least one supply hole 42b. When the fluid supply portion 42 includes a plurality of supply holes 42b, a plurality of different fluid samples may be simultaneously inspected in the fluid accommodating cartridge 40. Here, the plurality of different fluid samples may refer to a plurality of fluid samples having the same type and different sources. Alternatively, the plurality of different fluid samples may refer to a plurality of fluid samples having different types and different sources. Alternatively, the plurality of different fluid samples may refer to a plurality of fluid samples having the same type, the same source, and different states.

Since the housing 41 may contact a fluid sample while having a shape capable of implementing a specific function, the housing 41 may be formed of material that is easily molded and chemically and biologically inert. For example, the housing 41 may formed of various materials, including acrylic, such as polymethyl methacrylate (PMMA), polysiloxane, such as polydimethylsiloxane (PDMS), polycarbonate (PC), polyethylene, such as linear low density polyethylene (LLDPE), low density polyethylene (LDPE), Medium density polyethylene (MDPE), and high density polyethylene (HDPE), plastic material, such as polyvinyl alcohol, ultra-low density polyethylene (VLDPE), polypropylene (PP), acrylonitrile butadiene styrene (ABS), and cycloolefin copolymer (COC), glass, mica, silica, and semiconductor wafers. However, the materials are only examples of materials that may form the housing 41, and embodiments of the disclosure are not limited thereto, and any material having chemical and biological stability and mechanical processability can be used as a material of the housing 41 according to the embodiment of the disclosure.

The fluid accommodating cartridge 40 may be provided to allow the inspection unit 45 to be coupled or bonded thereto. In other words, the inspection unit 45 may be coupled or bonded to the housing 41. A fluid sample injected through the fluid supply portion 42 may flow into the inspection unit 45, and as a reaction between the fluid sample and the reagent occurs in the inspection unit 45, the inspection may proceed. The inspection unit 45 may include a well (or an inspection portion) in which a reagent to react with a fluid sample is accommodated. A plurality of wells may be provided in the inspection unit 45. The plurality of wells may be arranged in the inspection unit 45 in one or more rows. The plurality of wells may contain reagents that react with the fluid sample in advance.

Figure 4:
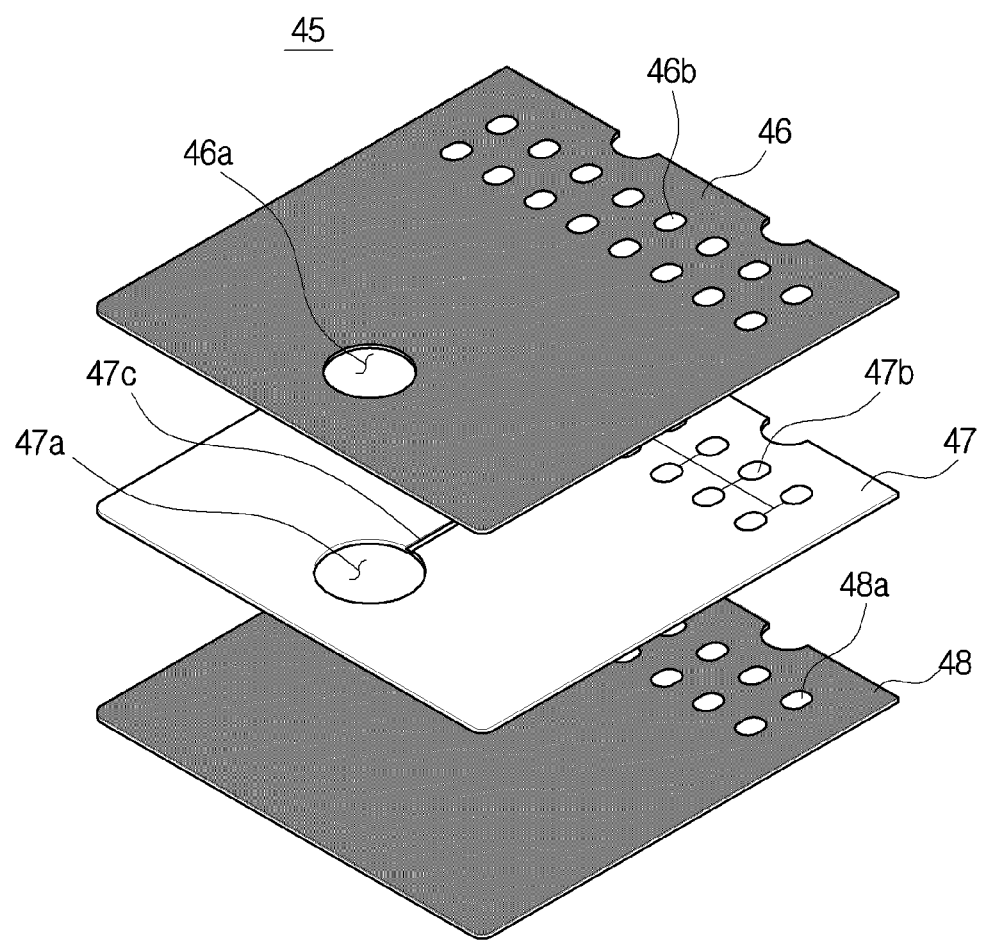
FIG. 4 is an exploded view illustrating an inspection unit of a fluid accommodating cartridge according to an embodiment of the disclosure.

FIG. 4 is an exploded view illustrating an inspection unit of a fluid accommodating cartridge according to an embodiment of the disclosure.

Referring to FIG. 4, the inspection unit 45 of the fluid accommodating cartridge 40 may have a structure in which three plates are bonded to each other. The three plates may include a first plate 46, a second plate 47, and a third plate 48. The first plate 46 and the third plate 48 are printed with a light-shielding ink to protect a fluid sample moving to a well 47b from external light or prevent errors from occurring when measuring optical properties in the well 47b. In addition, the first plate 46 and the third plate 48 may be coated with a light-shielding film to protect a fluid sample moving to the well 47b from external light or prevent errors from occurring when measuring optical properties in the well 47b. The light shielding film may include carbon. However, the first plate 46, the second plate 47, and the third plate 48 may be integrally formed with each other.

The films used to form the first plate 46 and the third plate 48 of the inspection unit 45 may include one selected from a polyethylene film, such as ultra-low density polyethylene (VLDPE), linear low density polyethylene (LLDPE), low density polyethylene (LDPE), medium density polyethylene (MDPE), and high density polyethylene (HDPE), a polypropylene (PP) film, a polyvinyl chloride (PVC) film, a polyvinyl alcohol (PVA) film, a polystyrene (PS) film, and a polyethylene terephthalate (PET) film. However, this is only an example, and the films forming the first plate 46 and the third plate 48 of the inspection unit 45 may be provided using any film of material that can be chemically and biologically inert and have mechanical processability.

Unlike the first plate 46 and the third plate 48, the second plate 47 of the inspection unit 45 may be formed of a porous sheet. Examples of the porous sheet that may be used as the second plate 47 include at least one of cellulose acetate, nylon, such as nylon 6.6 and nylon 6.10, polyethersulfone, poly tetrafluoro ethylene (PTFE), and poly vinylidene fluoride (PVDF). Since the second plate 47 is form of a porous sheet, the second plate 47 serves as a vent in itself, and allows a fluid sample to move within the inspection unit 45 without a separate driving source. In addition, when the fluid sample is hydrophilic, the second plate 47 having hydrophilicity may be coated with a hydrophobic solution to prevent the fluid sample from permeating into the second plate 47.

The first plate 46, the second plate 47, and the third plate 48 may have a stacked structure.

The first plate 46 may be disposed to face the second plate 47. The third plate 48 may be disposed to face the first plate 46 with the second plate 47 interposed therebetween. That is, the second plate 47 may be disposed between the first plate 46 and the third plate 48.

The first plate 46 is formed with a first inlet 46a through which a fluid sample is introduced, and a region 46b of the first plate 46 corresponding to the well 47b may be transparent. The first plate 46 may include at least one first inlet 46a through which a fluid sample is introduced. The third plate 48 also has a region 48a corresponding to the well 47b to be transparent such that the absorbance of a reaction occurring in the well 47b, that is, optical property is measured.

The second plate 47 is also formed with a second inlet 47a through which a fluid sample is introduced, and the first inlet 46a of the first plate 46 and the second inlet 47a of the second plate 47 overlap each other to form an inlet (not shown) of the inspection unit 45. The second plate 47 may be formed with at least one second inlet 47a for introducing a fluid sample while corresponding to the at least one first inlet 46a. The first inlet 46a may have a width narrower than that of the second inlet 47a. In other words, the at least one first inlet 46a may have a width narrower than that of the at least one second inlet 47a. In the inspection unit 45, various reactions for fluid analysis may occur, and when blood is used as a fluid sample, a reagent that develops or changes colors by reacting with a specific component of blood (e.g., plasma) is accommodated in the well 47b such that a color expressed in the well 47b may be optically detected and converted into a numeric value. Through the numeric value, the presence or absence of a specific component in the blood or the proportion of a specific component may be identified. In addition, a flow path 47c connecting the second inlet 47a to the well 47b may be formed in the second plate 47.

Figure 5:
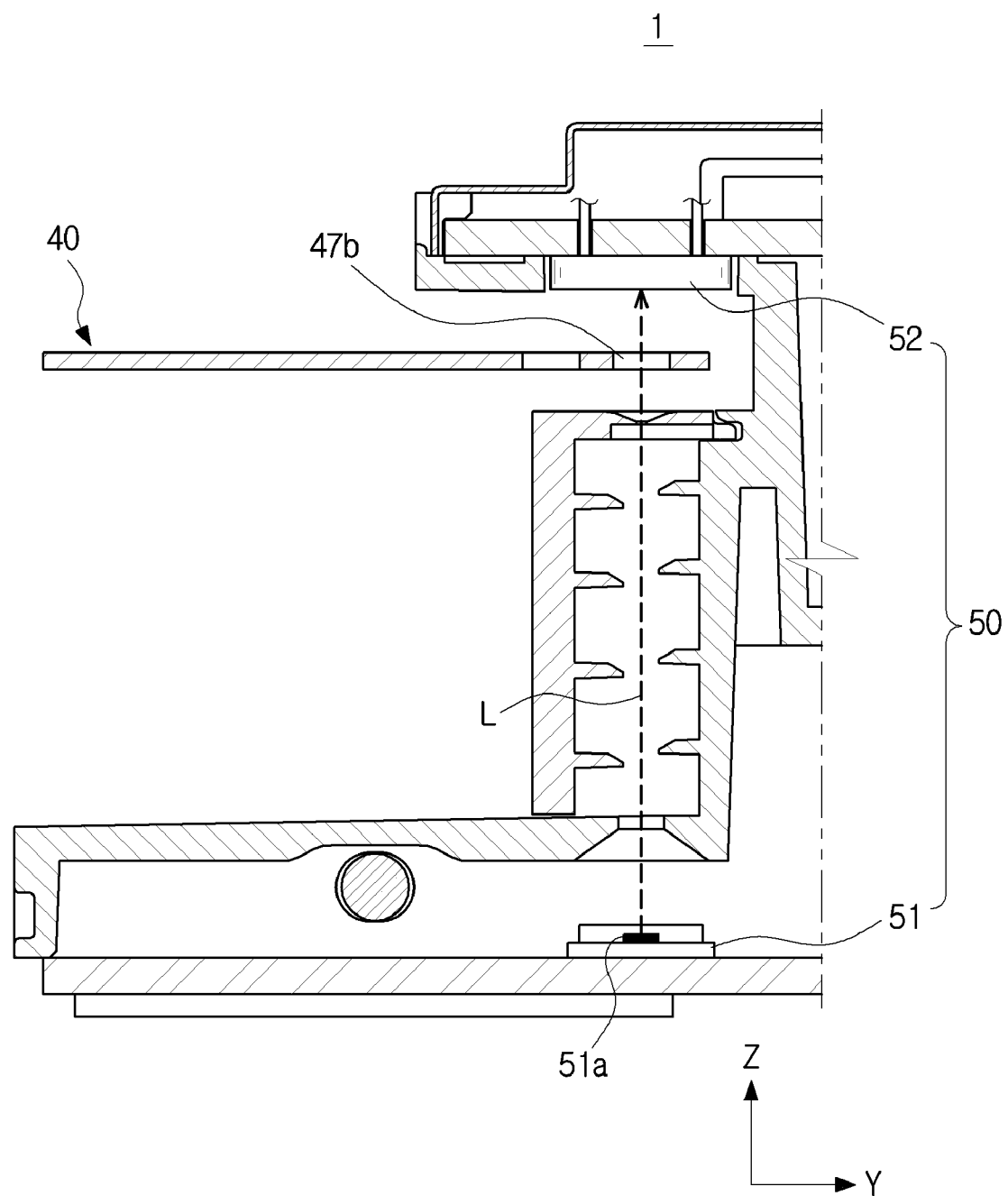
FIG. 5 is a cross-sectional view of a fluid analysis apparatus equipped with a fluid accommodating cartridge according to an embodiment of the disclosure.

FIG. 5 is a cross-sectional view of a fluid analysis apparatus equipped with a fluid accommodating cartridge according to an embodiment of the disclosure.

In FIG. 5, a measurement portion 50 may be provided to measure the well 47b of the fluid accommodating cartridge 40 with the fluid accommodating cartridge 40 interposed therebetween when the fluid accommodating cartridge 40 is mounted. In the disclosure, the measuring of the well of the fluid accommodating cartridge 40 by the measurement portion 50 refers to measuring the well prepared in the fluid accommodating cartridge 40, a fluid sample contained in the well, or a fluid reactant generated by reacting a fluid sample with a reagent.

In addition, the transmitting of light from the measurement portion 50 toward the well may include transmitting light toward the well or a fluid sample accommodated in the well. In addition, the detecting of the optical signal from the light passed through the well by the measurement portion may include detecting the optical signal from the light passed through the well or the fluid sample accommodated in the well.

The measurement portion 50 may include a light source portion 51 for transmitting light toward the well 47b and a light detection portion 52 for detecting light passing through the well 47b. The light source portion 51 and the light detection portion 52 are disposed to face each other, and the fluid accommodating cartridge 40 may be inserted between the light source portion 51 and the light detection portion 52.

The light source portion 51 and the light detection portion 52 may sequentially scan the wells 47b of the fluid accommodating cartridge 40 while moving together in one direction (hereinafter, referred to as a scan direction) (the X-axis direction) by a driving device (not shown). In another embodiment, the light source portion 51 and the optical detection portion 52 may be fixed, and the fluid accommodating cartridge 40 may allow the wells 47b to be sequentially scanned while moving.

The light source portion 51 may include a light source 51a that transmits light L onto the well 47b of the fluid accommodating cartridge 40. The light L transmitted from the light source 51a may be formed as a beam spot in the well 47b of the fluid accommodating cartridge 40, and the beam spot may be smaller than the diameter of the well 47b. The light L passed through the well 47b may be detected by the light detection portion 52. Meanwhile, the light source portion 51 may further include a lens for focusing light emitted from the light source 51a or an aperture (or a pin hole) for limiting the light flux.

In various embodiments, for accurate measurement of a fluid sample, it is important to accurately mount the fluid accommodating cartridge 40 in the correct position. That is, the fluid accommodating cartridge 40 needs to be mounted at the correct position so that the beam spot of the light L transmitted from the light source portion 51 is formed at the central portion of the well 47b. Alternatively, the fluid accommodating cartridge 40 needs to be mounted at the correct position so that the light L (e.g., the central axis of the light) transmitted from the light source portion 51 passes through the central portion of the well 47b. The central axis of the light L refers to an axis that becomes the center of the light, and may include a light axis, an optical axis, a main axis, or an axis having the greatest amount of light. In addition, when the light L is transmitted through the opening, the central axis of the light L is an axis that becomes the center of the light passing through the opening, and includes a light axis, an optical axis, a main axis, or an axis having the greatest amount of light passing through the opening. In addition, the central axis of light may refer to the central axis of light generating a beam spot formed on the well 47b.

In this case, the central portion of the well 47b may include the center of the well 47b or a region having a certain diameter or less from the center of the well 47b. For example, the central portion of the well 47b may include a region having a diameter of 35 um or less on the center of the well 47b. In order to form the beam spot of light at the central portion of the well 47b, the measurement portion 50 and the well 47b need to be aligned with each other. Here, the alignment may refer to having the center of the light source portion 51, the center of the light detection portion 52, and the center of the well 47b vertically in line with each other within an error range of a predetermined diameter. The predetermined diameter may be, for example, 100 um, 75 um, or 30 um, and preferably determined within a range of 30 um.

Figure 6:
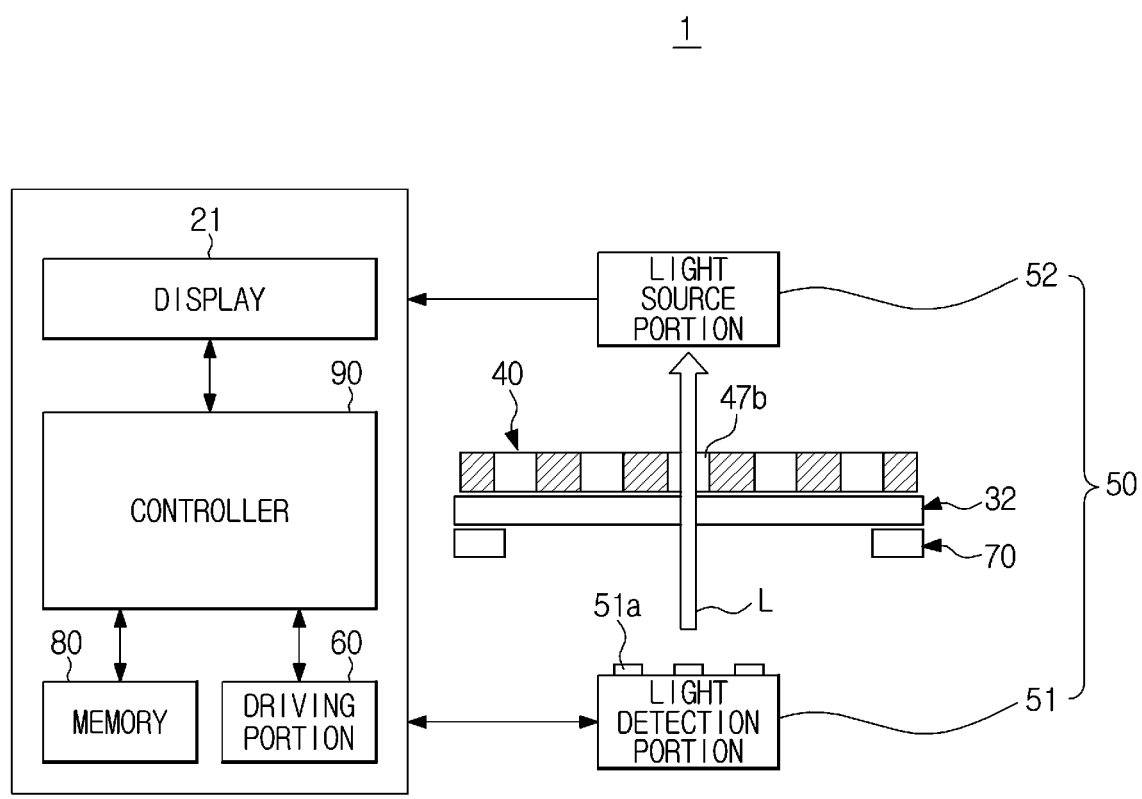
FIG. 6 is a block diagram illustrating a fluid analysis apparatus according to an embodiment of the disclosure.

FIG. 6 is a block diagram illustrating a fluid analysis apparatus according to an embodiment of the disclosure.

Referring to FIG. 6, the fluid analysis apparatus 1 includes the display 21, the measurement portion 50, the fluid accommodating cartridge 40, the mounting portion 32, a driving portion 60, an actuator 70, a memory 80, and a controller 90.

The display 21 may display information processed by the controller 90. For example, the display 21 may display fluid sample analysis content, fluid sample analysis operation status, and the like as the processed information. The display 21 may be implemented as a touch screen having a layer structure in combination with a touch panel (not shown). The touch screen may not only have a function of display but also have a function of detecting a touch input position, a touched area, and a touch input pressure. In addition, the display 21 may also have a function of detecting a real-touch as well as a proximity touch.

The measurement portion 50 may measure the well of the fluid accommodating cartridge 40. The measurement portion 50 may include the light source portion 51 and the light detection portion 52.

The light source portion 51 may include a light source 51a that transmits light L onto the well 47b of the fluid accommodating cartridge 40. The light source 51a may be, for example, a light source having a predetermined wavelength band selected from electromagnetic waves of various waves, such as microwaves, infrared rays, visible rays, ultraviolet rays, and X-rays. For example, the light source 51a may emit light in a wavelength band exhibiting a difference in optical properties according to the concentration of a sample accommodated in the fluid accommodating cartridge 40 or having a change in absorbance according to a reagent reaction. The light source 51a may be provided in one unit or a plurality of units thereof. When a plurality of light sources 51a are provided, the light sources 51a may have different wavelength bands. In this case, the fluid analysis apparatus 10 may perform multi-item simultaneous inspection by simultaneously measuring optical properties for a plurality of wavelengths on a fluid sample contained in the fluid accommodating cartridge 40.

The light source portion 51 may additionally include a sub-light source. The sub-light source may emit light in a wavelength band exhibiting a constant optical characteristic regardless of the concentration of the fluid sample in the fluid accommodating cartridge 40 or having no change in absorbance according to a reagent reaction. The sub-light source may be used to determine whether the fluid accommodating cartridge 40 is mounted or whether the fluid accommodating cartridge 40 is incorrectly mounted. Further, the sub-light source may be used to correct an error generated in the measurement result of the light source 51a.

The light detection portion 52 may detect light L transmitted through the well 47b of the fluid accommodating cartridge 40. The light detection portion 52 may include a light receiving element, such as a photodiode and an image sensor.

The fluid accommodating cartridge 40 may include one or more wells 47b in which a fluid sample is received.

The mounting portion 32 may fix the inserted fluid accommodating cartridge 40.

The driving portion 60 may drive and control the light source portion 51 and the light detection portion 52. For example, the driving portion 60 may move at least one of the light source portion 51 or the light detection portion 52 in one direction (the X-axis direction) so that the light source portion 51 and the light detection portion 52 sequentially scan the wells 47b of the fluid accommodating cartridge 40.

The actuator 70 may be provided on one part of the fluid analysis apparatus 1. For example, the actuators 70 may be provided on both sides of the body (32e in FIG. 2A) of the mounting portion 32. In particular, when the mounting portion 32 includes a supporting portion (32f in FIG. 7A) for supporting the mounting portion 32 on the fluid analysis apparatus 1, the actuator 70 may be provided at a lower side of the supporting portion (32f in FIG. 7A).

The actuator 70 may include, for example, a microactuator. The micro-actuator may include, for example, an auto focusing voice coil motor (AF VCM), an optical image stabilizer voice coil motor (OIS VCM), or a piezo actuator. The AF VCM is a micro actuator mainly used to finely move a lens to adjust the focus of a camera. The OIS VCM is a micro-actuator mainly used to correct a person's hand-shake during shooting. The piezo actuator is an actuator that uses properties of a material in which the length of the electric field changes in response to application of electricity, and is mainly used for ink jetting of a printer.

The AF VCM, the OIS VCM, and the piezo actuators are characterized in small size, high precision, and short stroke. Such features may be suitable for fine-tuning operations for aligning the measurement portion 50 with the well 47b. Meanwhile, in addition to the above described AF VCM, OIS VCM, and piezo actuator, various types of actuators 70 may be used as long as it can have the above-described characteristics for aligning the measurement portion 50 with the well 47b according to the disclosure.

The controller 90 may include one or more processors. The controller 90 may control at least one other component of the fluid analysis apparatus 1 connected to the processor (e.g., the measurement portion 50, the driving portion 60, the actuator 70, or the display 21) and perform various data processing and calculations by driving software. The controller 90 may load commands or data received from other components (e.g., the measurement portion 50) onto the memory 80 and process the commands or data. For example, the controller 90 may process optical signals measured by the measurement portion 50.

In one embodiment, the controller 90 may control the operation of the actuator 70 based on the optical signal detected by the measurement portion 50 such that light transmitted from the measurement portion 50 passes through the central portion of the well 47b, so that an accurate inspection of the fluid sample is performed. The controller 90 may control the operation of the actuator 70 such that the measurement portion 50 and the well 47b are aligned with each other in order for the light to pass through the central portion of the well 47b. In addition, the controller 90 may control the operation of the actuator 70 such that the center of the light source portion 51, the center of the light detection portion 52, and the center of the well 47b are vertically in line with each other in an error range of a predetermined diameter.

In one embodiment, when the actuator 70 is provided in the mounting portion 32 or the measurement portion 50, the controller 90 controls the operation of the actuator 70 to move the mounting portion 32 or the measuring part 50 such that a beam spot of light is formed at the central portion of the well 47b. For example, the controller 90 may control the operation of the actuator 70 to move the pin hole portion included in the measurement portion 50.

In one embodiment, the controller 90 may control the operation of the actuator 70 based on the width of the optical signal. For example, when the width of the optical signal is outside an allowable range, the controller 90 identifies that the fluid accommodating cartridge 40 is abnormally mounted, and controls the operation of the actuator 70 such that the width of the optical signal is within the allowable range. In addition, when it is identified that the fluid accommodating cartridge 40 is abnormally mounted, the controller 90 identifies the direction of mis-installation of the fluid accommodating cartridge 40 by controlling the operation of the actuator 70, and controls the operation of the actuator 70 such that the width of the optical signal is within the allowable range based on the mis-installation direction.

In one embodiment, the controller 90 may control the operation of the actuator 70 based on the strength of the optical signal. For example, when the strength of the optical signal is outside an allowable range, the controller 90 identifies that the fluid accommodating cartridge 40 is abnormally mounted, and controls the operation of the actuator 70 such that the strength of the optical signal is within the allowable range. In addition, when it is identified that the fluid accommodating cartridge 40 is abnormally mounted, the controller 90 identifies the direction of mis-installation of the fluid accommodating cartridge 40 by controlling the operation of the actuator 70, and controls the operation of the actuator 70 such that the strength of the optical signal is within the allowable range based on the mis-installation.

In one embodiment, the measurement portion 50 may transmit light to at least one of the well 47b or the slit provided in the fluid accommodating cartridge 40, and detect an optical signal from light transmitted through the at least one of the well 47b or the slit.

In one embodiment, when a plurality of actuators 70 are provided in the mounting portion 32, the controller 90 may move the mounting portion 32 upward, downward, clockwise, or counterclockwise by controlling the plurality of actuators 70.

The memory 80 may store various pieces of data used by at least one component of the fluid analysis apparatus 1, for example, software and input data or output data regarding commands related to the software. The memory 80 may include a volatile memory or a nonvolatile memory.

For example, the memory 80 may store optical signals measured by the measurement portion 50. In addition, the memory 80 may store information regarding an operation pattern, an operation range, and an operation direction for the operation of the actuator 70. In addition, the memory 80 may store the width or strength value of the optical signal determined as a reference, which will be described below in FIGS. 11A to 12D, and may store information about an allowable range for determining whether alignment between the measurement portion 50 and the well 47b is successful or not.

FIGS. 7A to 8B are views illustrating an interior of a fluid analysis apparatus according to an embodiment of the disclosure.

Figure 7A:
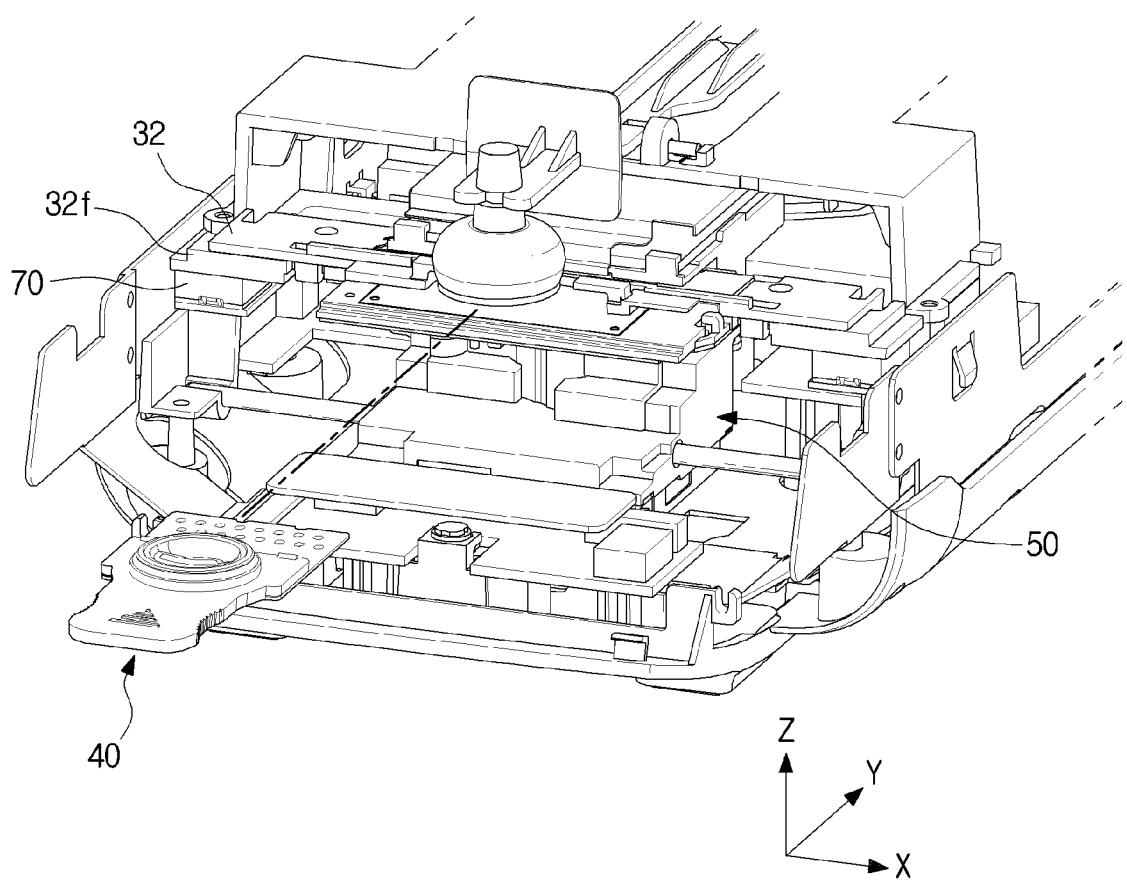
FIGS. 7A to 8B are views illustrating an interior of a fluid analysis apparatus according to an embodiment of the disclosure.
Figure 7B:
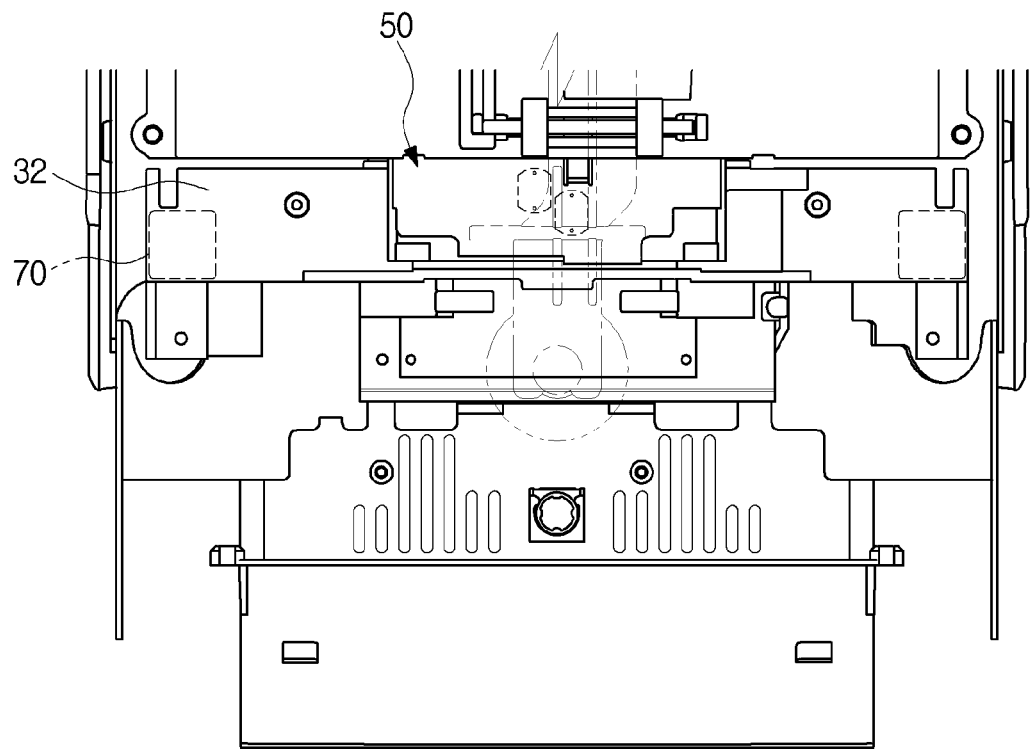
Figure 7B:
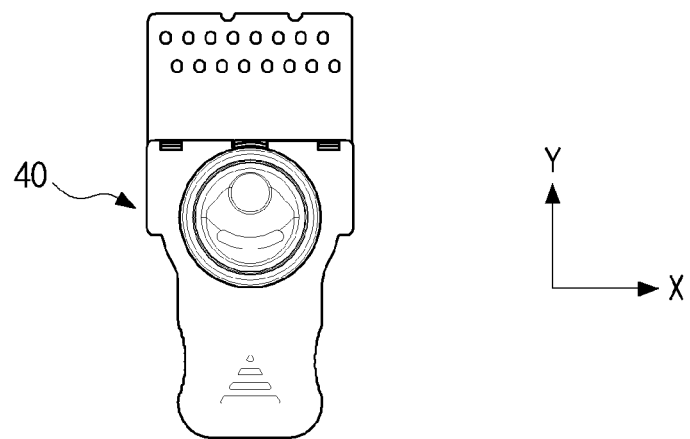
Figure 8A:
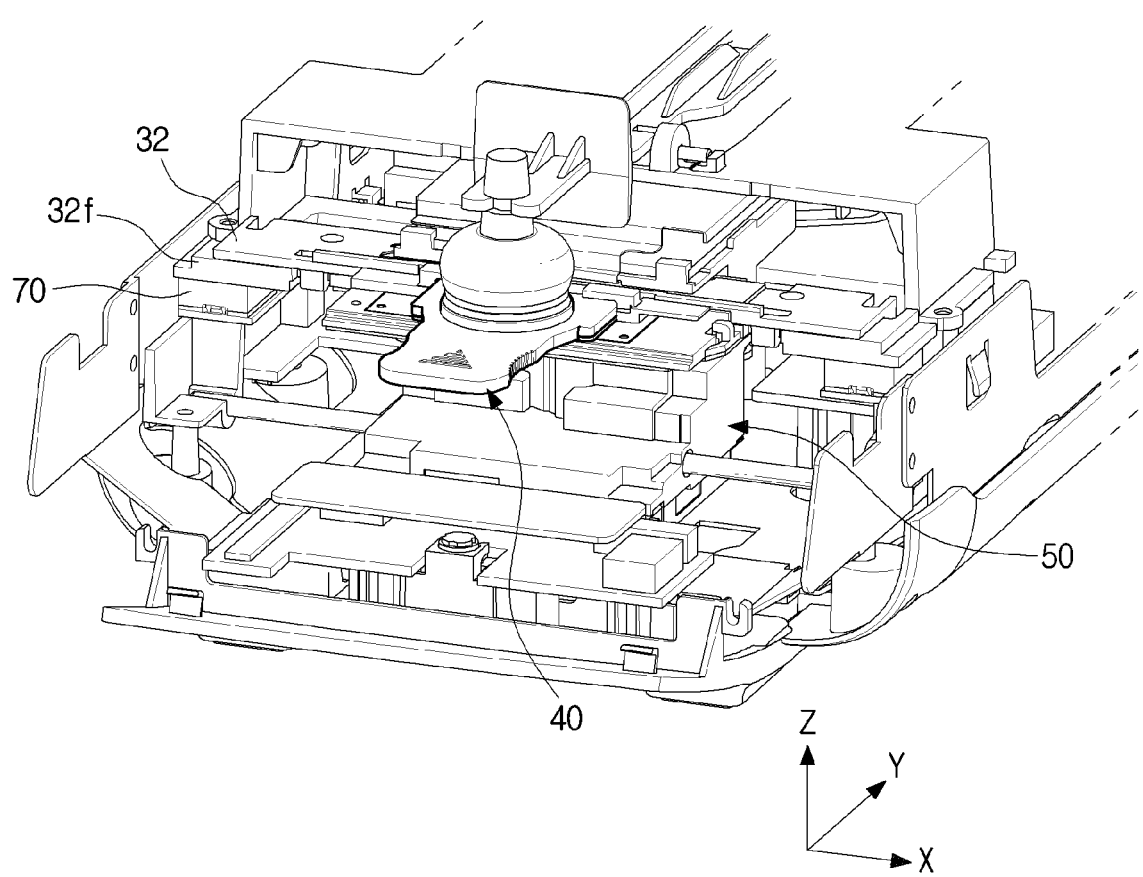
Figure 8B:
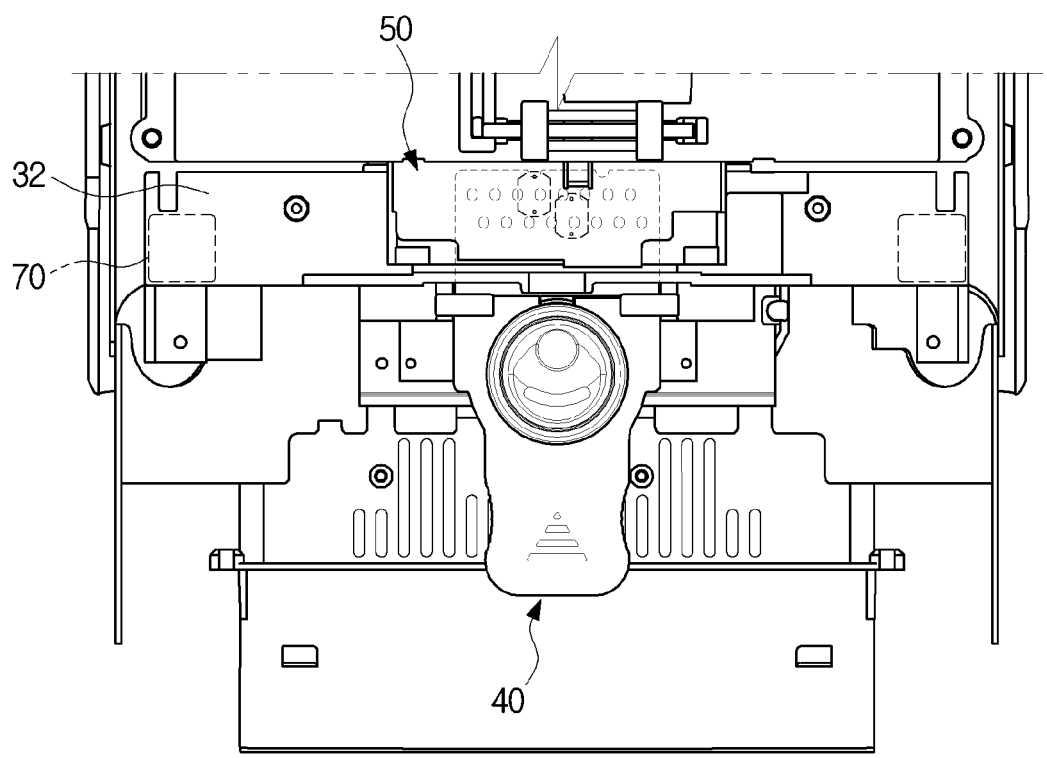

FIGS. 7A and 7B illustrate a perspective view and a plan view showing a state in which the mounting portion 32 and the fluid accommodating cartridge 40 of the fluid analysis apparatus 1 are disassembled. FIGS. 8A and 8B illustrate a perspective view and a plan view showing a state in which the mounting portion 32 and the fluid accommodating cartridge 40 of the fluid analysis apparatus 1 are assembled.

Referring to FIGS. 7A to 8B, a plurality of actuators 70 may be provided below both sides of the mounting portion 32. Specifically, when the mounting portion 32 includes the support portion 32f, the actuator 70 may be provided below the support portion 32f.

Referring to 7A to 8B, a plurality of actuators 70 are illustrated as being provided below both sides of the mounting portion 32, but one or more actuators 70 may be provided at various positions of the fluid analysis apparatus 10.

For example, the actuator 70 may be provided on one side of the mounting portion 32, and a support having a size corresponding to the height of the actuator 70 may be provided on the other side of the mounting portion 32.

As another example, the actuator 70 may be provided at any region of the body 32e of the mounting portion 32. For example, at least one actuator 70 may be provided in one region between a region where the fluid accommodating cartridge 40 is mounted and both sides of the mounting portion 32.

FIGS. 9A to 10B are views illustrating a moving direction of the mounting portion 32 by the actuator 70 according to an embodiment of the disclosure.

Referring to FIGS. 9A to 10B, the measurement portion 50 may measure the wells 47b of the fluid accommodating cartridge 40 while moving in the scan direction (the X-axis direction).

For accurate measurement of the wells 47b, the fluid analysis apparatus 1 may control the actuator 70 (70a or 70b) such that the measurement portion 50 and the wells 47b of the fluid accommodating cartridge 40 are aligned. According to the control of the actuator 70, the mounting portion 32 on which the fluid accommodating cartridge 40 is mounted may be moved.

Figure 9A:
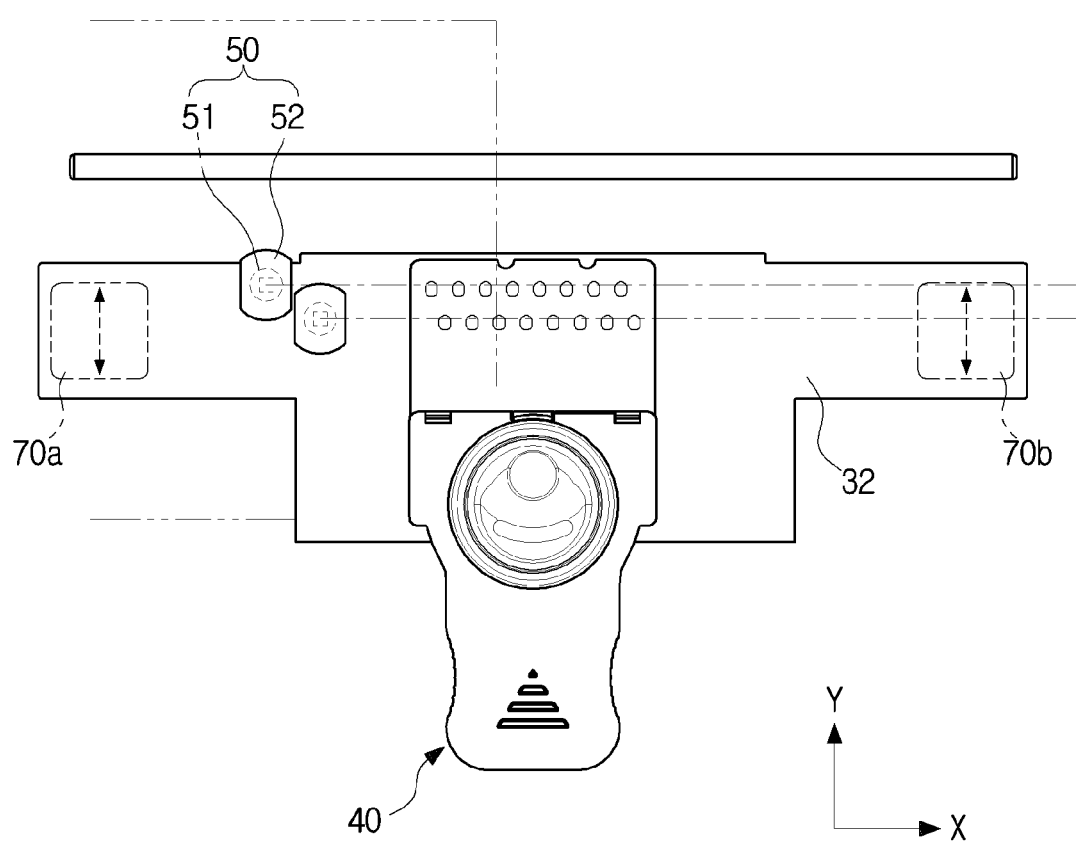
FIGS. 9A to 10B are views illustrating a moving direction of a mounting portion by an actuator according to an embodiment of the disclosure.

In FIG. 9A, the plurality of actuators 70a and 70b may have a degree of freedom of driving in one axis (the Y-axis direction).

Figure 9B:
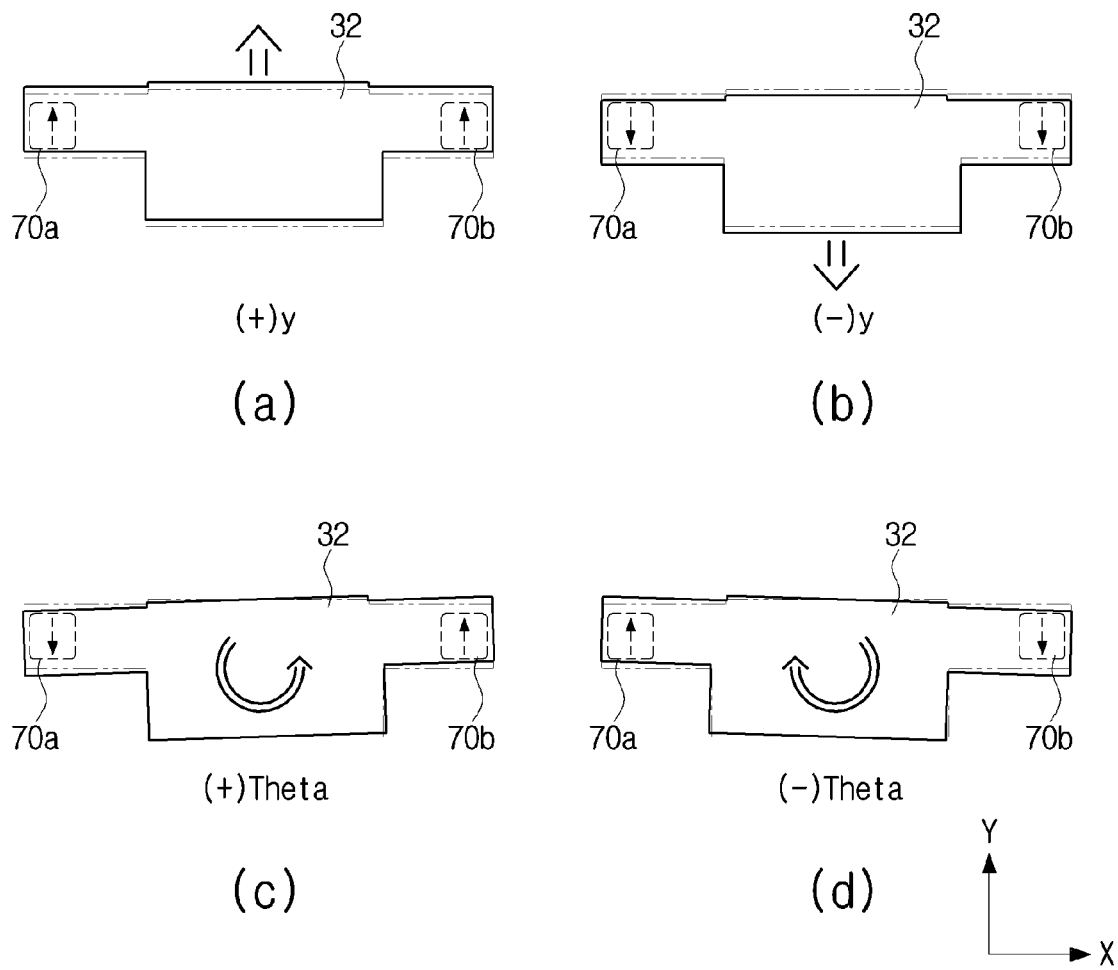

In this case, according to the control of the plurality of actuators 70a and 70b, the mounting portion 32 may be moved in various directions as shown in FIG. 9B.

For example, as illustrated in (a) of FIG. 9B, when all of the control directions of the plurality of actuators 70a and 70b are the upward direction of the Y-axis, the mounting portion 32 may be moved upward in the Y-axis. Alternatively, as illustrated in (b) of FIG. 9B, when all of the control directions of the plurality of actuators 70a and 70b are the downward direction of the Y-axis, the mounting portion 32 may be moved downward in the Y-axis. Alternatively, as illustrated in (c) of FIG. 9B, when the control direction of one actuator 70a is the downward direction of the Y-axis, and the control direction of the other actuator 70b is the upward direction of the Y-axis, the mounting portion 32 may move counterclockwise by an angle of theta. Alternatively, as illustrated in (d) of FIG. 9B, when the control direction of one actuator 70a is the upward direction of the Y-axis, and the control direction of the other actuator 70b is the downward direction of the Y-axis, the mounting portion 32 may move clockwise by an angle of theta (negative theta).

Figure 10A:
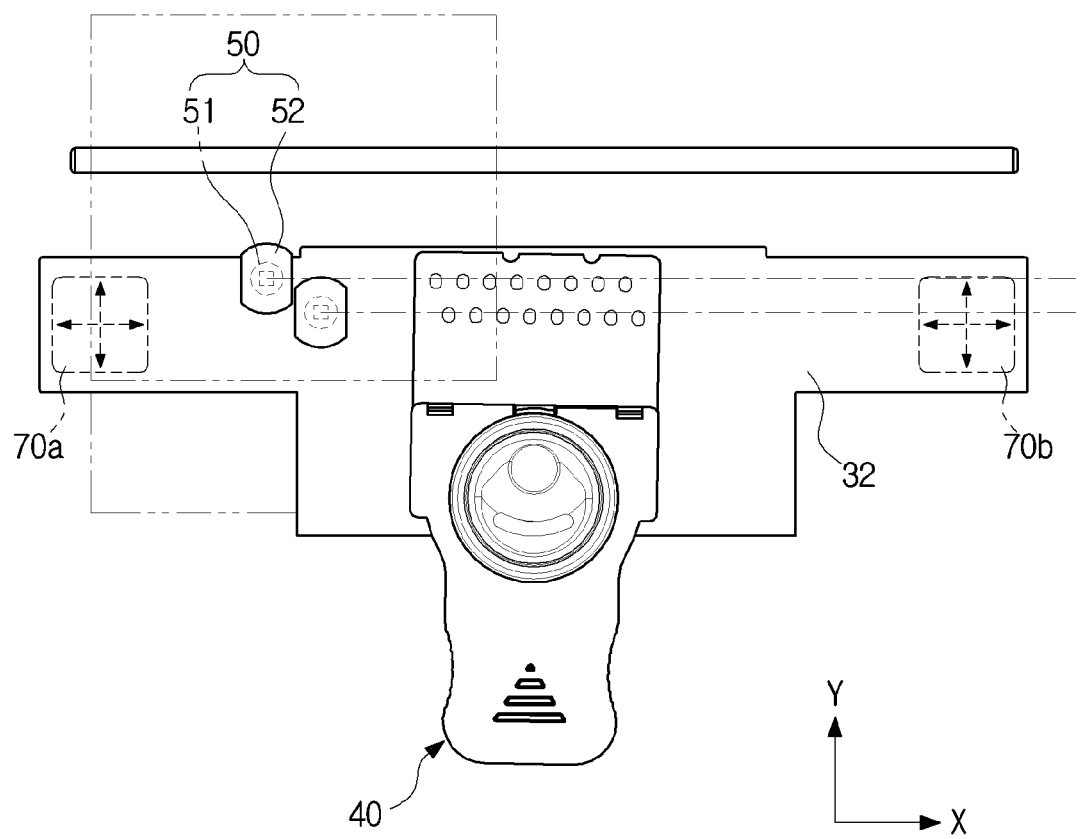

In FIG. 10A, the plurality of actuators 70a and 70b may have degrees of freedom of driving in multiple axes (the Y-axis direction and the Y-axis direction).

Figure 10B:
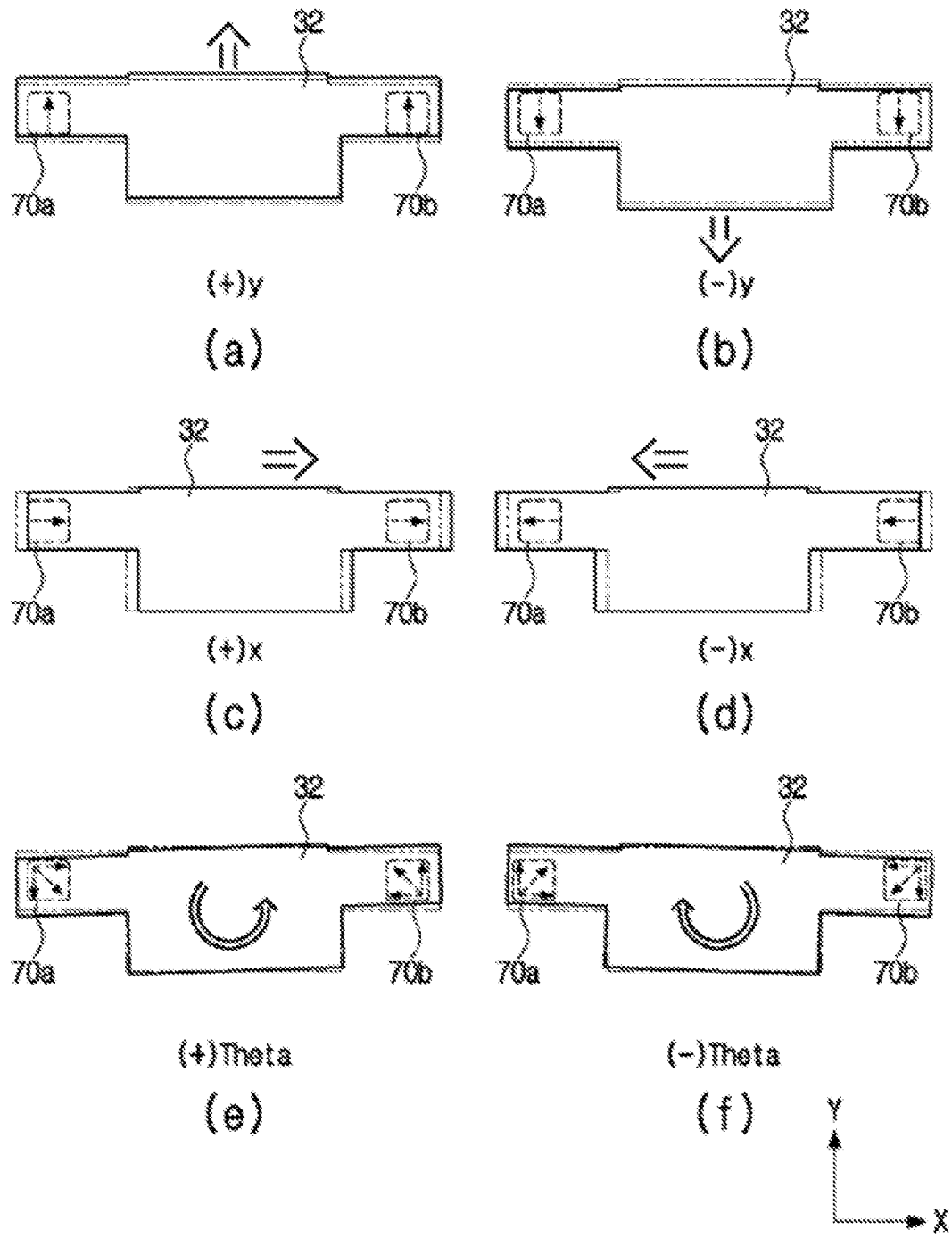

In this case, according to the control of the plurality of actuators 70a and 70b, the mounting portion 32 may be moved in various directions as illustrated in FIG. 10B.

For example, as illustrated in (a) of FIG. 10B, when all of the control directions of the plurality of actuators 70a and 70b are the upward direction of the Y-axis, the mounting portion 32 may be moved upward in the Y-axis. Alternatively, as illustrated in (b) of FIG. 10B, when all of the control directions of the plurality of actuators 70a and 70b are the downward direction of the Y-axis, the mounting portion 32 may be moved downward in the Y-axis. Alternatively, as illustrated in (c) of FIG. 10B, when all of the control directions of the plurality of actuators 70a and 70b are the right direction of the X-axis, the mounting portion 32 may be moved in the right direction of the X-axis. Alternatively, as illustrated in (d) of FIG. 10B, when all of the control directions of the plurality of actuators 70a and 70b are the left direction of the X-axis, the mounting portion 32 may be moved in the left direction of the X-axis. Alternatively, as illustrated in (e) of FIG. 10B, when the control direction of one actuator 70a is a diagonal direction between the downward direction of the Y-axis and the right direction of the X-axis, and the control direction of the other actuator 70b is a diagonal direction between the upward direction of the Y-axis and the left direction of the X-axis, the mounting portion 32 may move in the counterclockwise direction by an angle of positive theta. Alternatively, as illustrated in (f) of FIG. 10B, the control direction of one actuator 70a is a diagonal direction between the upward direction of the Y-axis and the right direction of the X-axis, and the control direction of the other actuator 70b is a diagonal direction between the downward direction of the Y-axis and the left direction of the X-axis, the mounting portion 32 may move in the clockwise direction by an angle of negative theta.

In this case, the theta value moved by the mounting portion 32 counterclockwise or clockwise in FIGS. 10A and 10B may have a magnitude greater than that of the theta value moved by the mounting portion 32 counterclockwise or clockwise in FIGS. 9A and 9B. That is, the use of a plurality of actuators 70a and 70b having degrees of freedom of multi-axis driving enables alignment of a larger angle.

FIGS. 11A to 12D are views illustrating alignment performed by controlling the actuator based on optical signals according to the embodiment of the disclosure.

FIGS. 11A to 12D describe control of the actuator based on optical signals measuring two wells, but it should be understood that the actuator may be controlled based on optical signals measuring three or more wells according to an implementation method.

FIGS. 11A to 11D illustrate a process of controlling the actuator such that the measurement portion 50 and the wells 47b are aligned based on the width (or the amount of light) of the optical signal detected by the measurement portion 50.

Figure 11A:
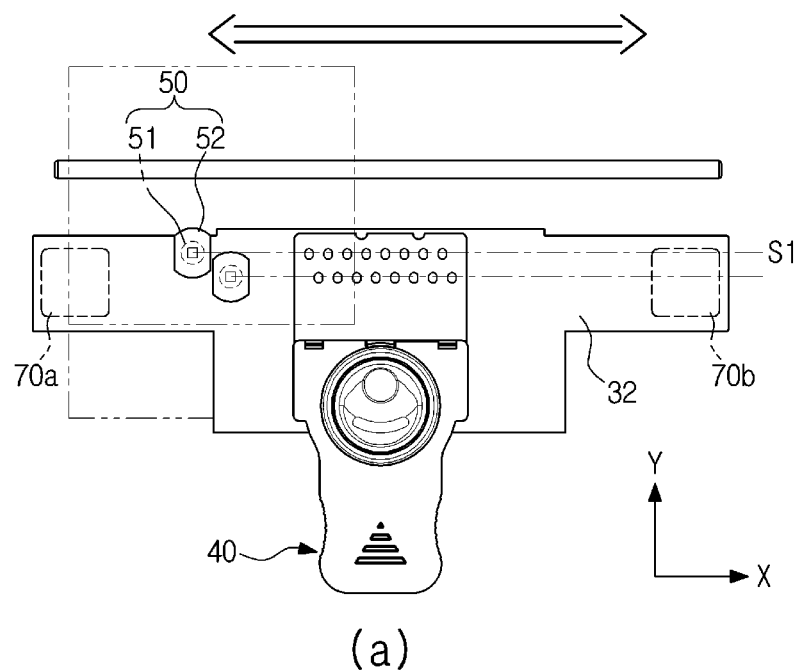
FIGS. 11A to 12D are views illustrating alignment performed by controlling an actuator according to an embodiment of the disclosure.
Figure 11A:
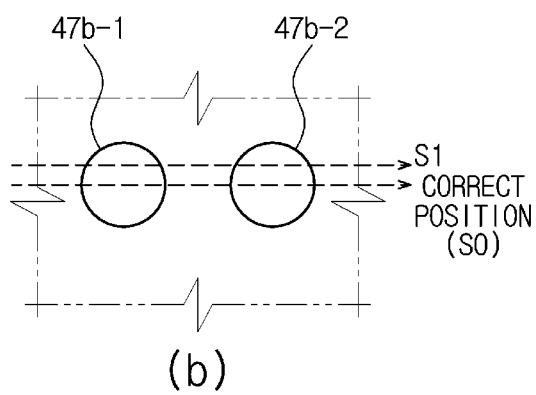
Figure 11A:
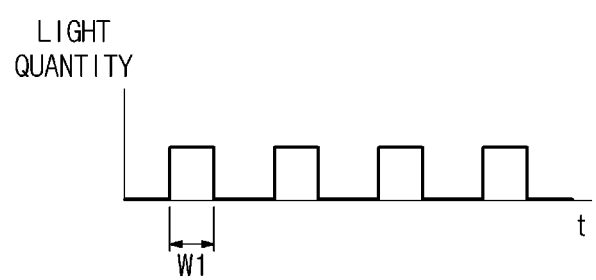

First, as illustrated in (a) of FIG. 11A, the fluid accommodating cartridge 40 may be normally mounted on the fluid analysis apparatus 1. In this case, as illustrated in (b) of FIG. 11A, a scan direction S0 of the measurement portion 50 may proceed to pass through the central portion of a first well 47b-1 and the central portion of a second well 47b-2. In this case, an optical signal related to the first well 47b-1 and the second well 47b-2 measured by the measurement portion 50 may have a width W0 as illustrated in (c) of FIG. 11A.

Figure 11B:
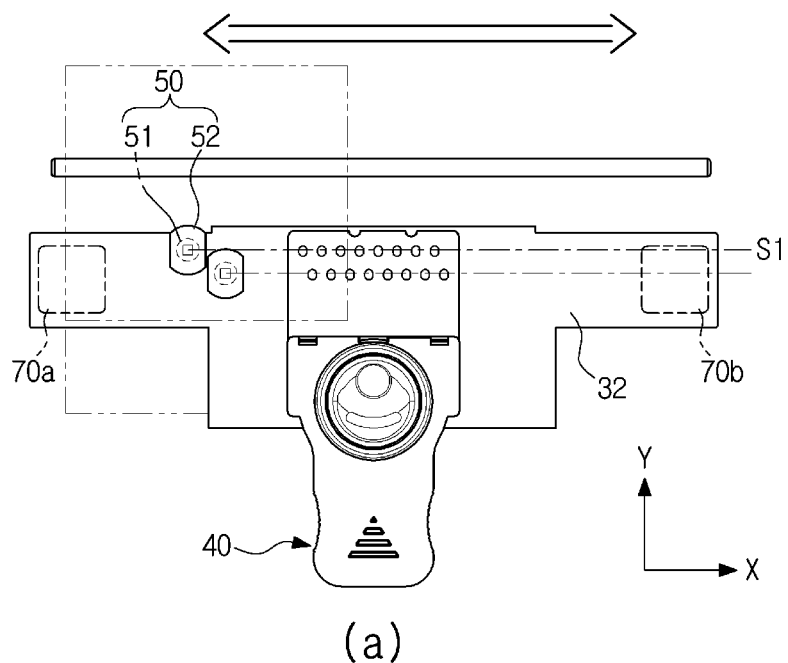
Figure 11B:
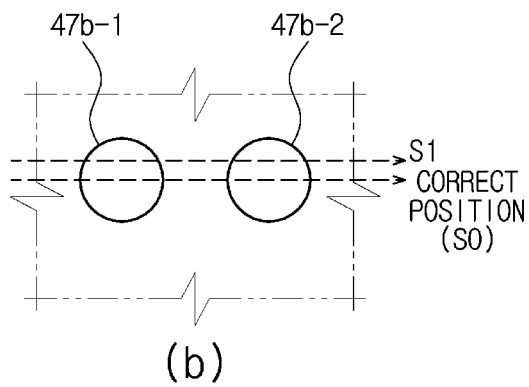
Figure 11B:
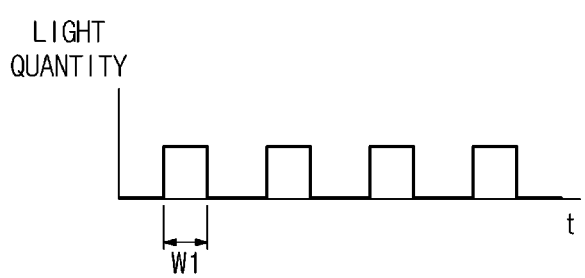

On the other hand, as illustrated in (a) of FIG. 11B, the fluid accommodating cartridge 40 may be abnormally mounted to the fluid analysis apparatus 1. In this case, as illustrated in (b) of FIG. 11B, a scan direction S1 of the measurement portion 50 may proceed to deviate from the central portion of the first well 47b-1 and the central portion of the second well 47b-2. In this case, an optical signal related to the first well 47b-1 and the second well 47b-2 measured by the measurement portion 50 may have a width W1 as shown in (c) of FIG. 11B.

The fluid analysis apparatus 1 may identify whether the fluid accommodating cartridge 40 is normally mounted in FIG. 11B based on the width W0 of the optical signal obtained when the fluid accommodating cartridge 40 is normally mounted as in FIG. 11A.

For example, when the fluid accommodating cartridge 40 is abnormally mounted, the width W1 of the optical signal measured in FIG. 11B may have a value different from that of the width W0 of the optical signal measured in FIG. 11A when the fluid accommodating cartridge 40 is normally mounted.

For example, an average value (or an average value of absolute values) for the widths W1 of the optical signal measured in FIG. 11B, a maximum value for the widths W1 of the optical signal measured in FIG. 11B, or a sum value of the widths W1 of the optical signal measured in FIG. 11B may be different from the values for the widths W0 of the optical signal measured when the fluid accommodating cartridge 40 is normally mounted as in FIG. 11A. For example, the average value for the widths W1 of the optical signal in FIG. 11B may be smaller than the average value for the widths W0 of the optical signal in FIG. 11A.

Accordingly, the fluid analysis apparatus 1 identifies that the fluid analysis cartridge 40 is abnormally mounted when the difference in the width of the optical signal is outside a preset allowable range, and identifies that the fluid analysis cartridge 40 is normally mounted when the difference in the width of the optical signal is within the preset allowable range.

Meanwhile, in FIG. 11B, the fluid analysis apparatus 1 may identify whether the fluid accommodating cartridge 40 is abnormally mounted, but may have difficulty in identifying in which direction the fluid accommodating cartridge 40 is deviated.

Figure 11C:
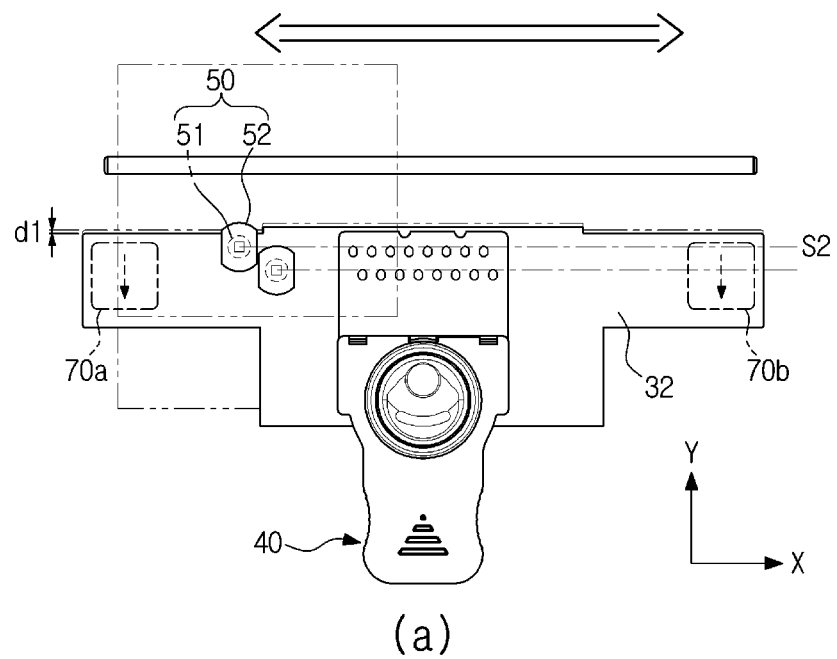
Figure 11C:
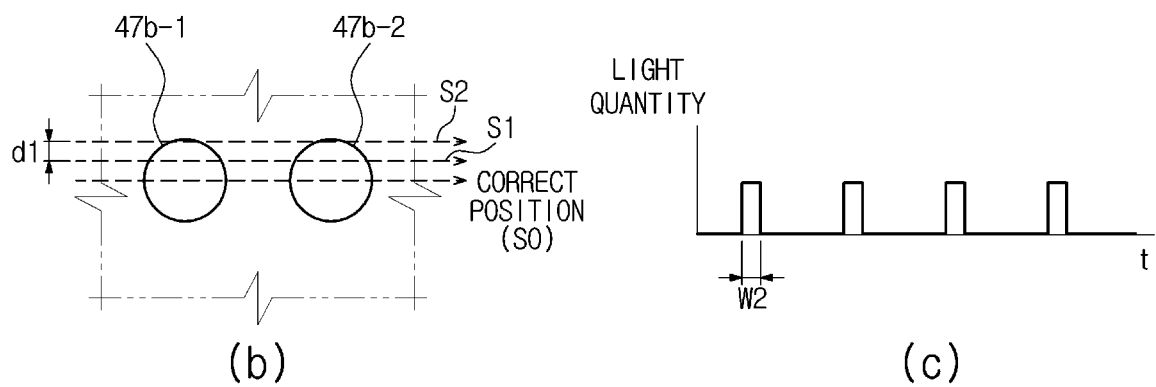

As illustrated in (a) of FIG. 11C, in order to identify the mis-installation direction of the fluid accommodating cartridge 40, the fluid analysis apparatus 1 controls the actuators 70a and 70b to move the mounting portion 32 by a predetermined distance d1 in a predetermined direction (the downward direction of the Y-axis). In this case, as illustrated in (b) of FIG. 11C, a rescan direction S2 of the measurement portion 50 may further deviate from the central portion of the first well 47b-1 and the central portion of the second well 47b-2. In this case, the optical signals related to the first well 47b-1 and the second well 47b-2 measured by the measurement portion 50 have a width W2 of as shown in (c) of FIG. 11C.

As a result of the rescan, the width W2 of the optical signal measured in FIG. 11C may be narrower than the width W1 of the optical signal measured in FIG. 11B. Accordingly, the fluid analysis apparatus 1 may determine that the fluid accommodating cartridge 40 is deviated in the downward direction of the y-axis in comparison to a case in which the fluid analysis cartridge 40 is normally mounted.

On the other hand, as a result of the rescan of the first well 47b-1 and the second well 47b-2, the width W2 of the optical signal measured in FIG. 11C is larger than the width W1 of the optical signal measured in FIG. 11B, the fluid analysis apparatus 1 may determine that the fluid accommodating cartridge 40 is deviated in the upward direction of the y-axis in comparison to a case in which the fluid analysis cartridge 40 is normally mounted.

When the mis-installation direction of the fluid accommodating cartridge 40 is identified, the fluid analysis apparatus 1 may control the operation of the actuators 70a and 70b such that the width of the optical signal related to the first well 47b-1 and the second well 47b-2 is within the allowable range based on the mis-installation direction.

Figure 11D:
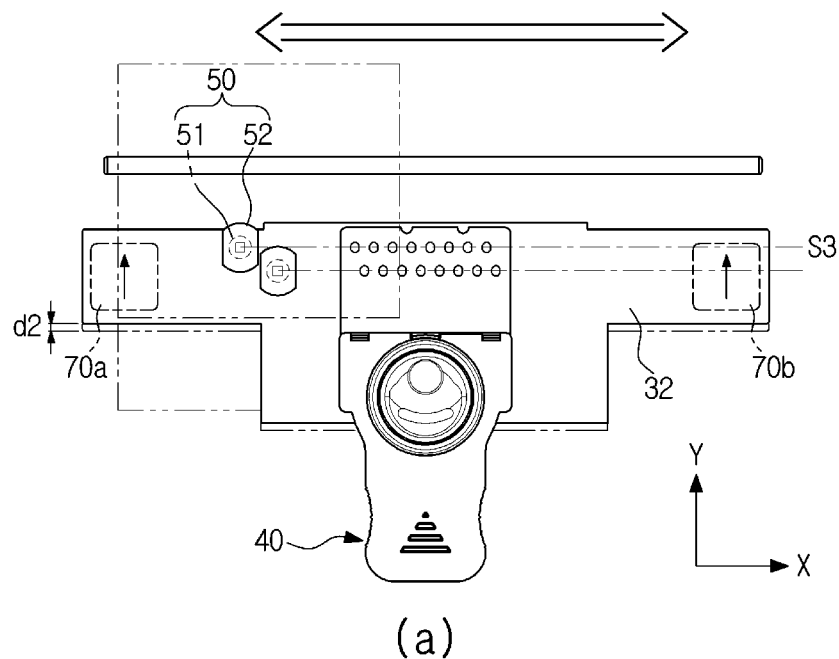
Figure 11D:
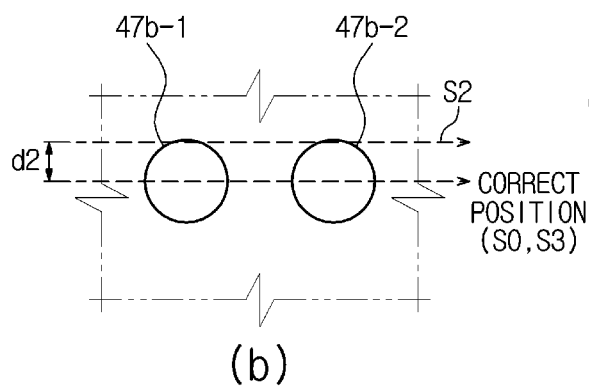
Figure 11D:
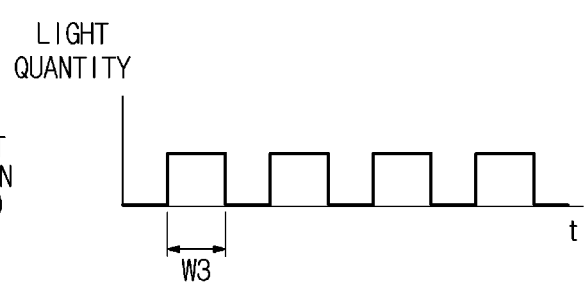

When it is identified that the fluid accommodating cartridge 40 is deviated in the upward direction in FIG. 11C, the fluid analysis apparatus 1 may move the fluid accommodating cartridge 40 in a predetermined direction (the downward direction of the Y-axis) by a predetermined distance d2 as shown in (a) of FIG. 11D. Then, in order to confirm that the fluid accommodating cartridge 40 is normally mounted, the fluid analysis apparatus 1 may sequentially re-scan the wells of the fluid accommodating cartridge 40 as shown in (b) of FIG. 11D. When the fluid accommodating cartridge 40 is normally mounted, the rescan direction S3 of the measurement portion 50 may pass through the central portion of the first well 47b-1 and the central portion of the second well 47b-2. In addition, in this case, in FIG. 11D, the optical signal related to the first well 47b-1 and the second well 47b-2 measured by the measurement portion 50 may have a width W3 that is equal or close to the width W0 of the optical signal shown in FIG. 11A.

When it is identified that the width W3 of the optical signal measured in FIG. 11D is within the allowable range in comparison to the width W0 of the optical signal obtained when the fluid accommodating cartridge 40 is normally mounted in FIG. 11A, the fluid analysis apparatus 1 may determine that the fluid accommodating cartridge 40 is normally mounted. Accordingly, the fluid analysis apparatus 1 may end the alignment procedure and perform a subsequent procedure for inspecting and analyzing the fluid sample accommodated in the fluid accommodating device 1.

FIGS. 12A to 12D are diagrams illustrating a process of controlling the actuator based on the strength (or the amount of light) of the optical signal detected by the measurement portion 50.

To this end, the fluid accommodating cartridge 40 may include at least one slit as a groove through which the optical signal is transmitted. When the slit is provided in plural, the plurality of slits 1201a and 1201b may be located on both sides of the fluid accommodating cartridge 40. Alternatively, a single slit may be located only on one side of the fluid accommodating cartridge 40. The groove through which the optical signal is transmitted may have various shapes as well as a rectangle. For example, the groove may have various shapes, such as a polygonal shape or a circular shape, and the edge of the groove may have a round shape.

Figure 12A:
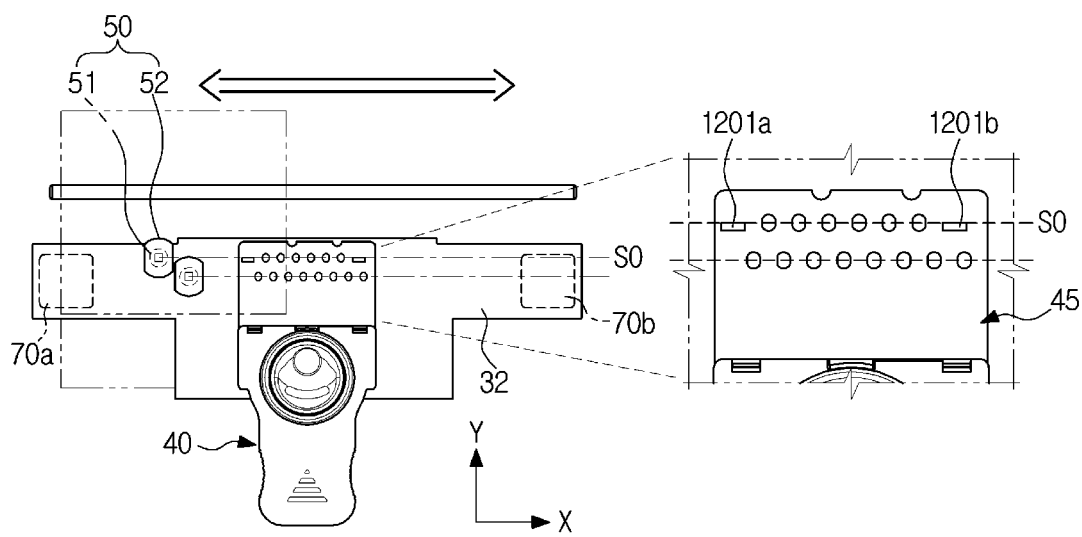
Figure 12A:
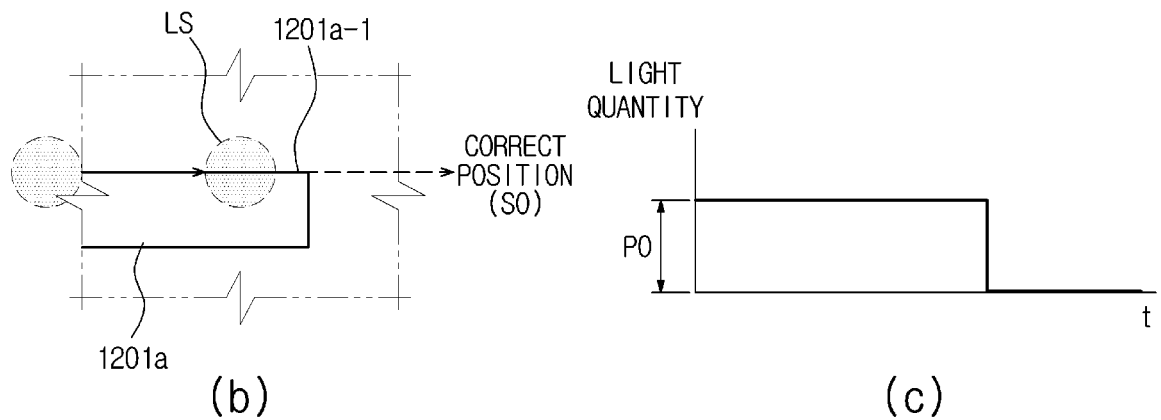

First, as illustrated in (a) of FIG. 12A, the fluid accommodating cartridge 40 may be normally mounted on the fluid analysis apparatus 1. In this case, as illustrated in (b) of FIG. 12A, a scanning direction S0 of the measurement portion 50 may proceed such that a central portion of a beam spot LS of light transmitted by the light source 51 passes through one surface 1201a-1 of the slit 1201a. In this case, the optical signal related to the slit 1201a measured by the measurement portion 50 may have a strength P0 as shown referring to (c) of FIG. 12A.

Figure 12B:
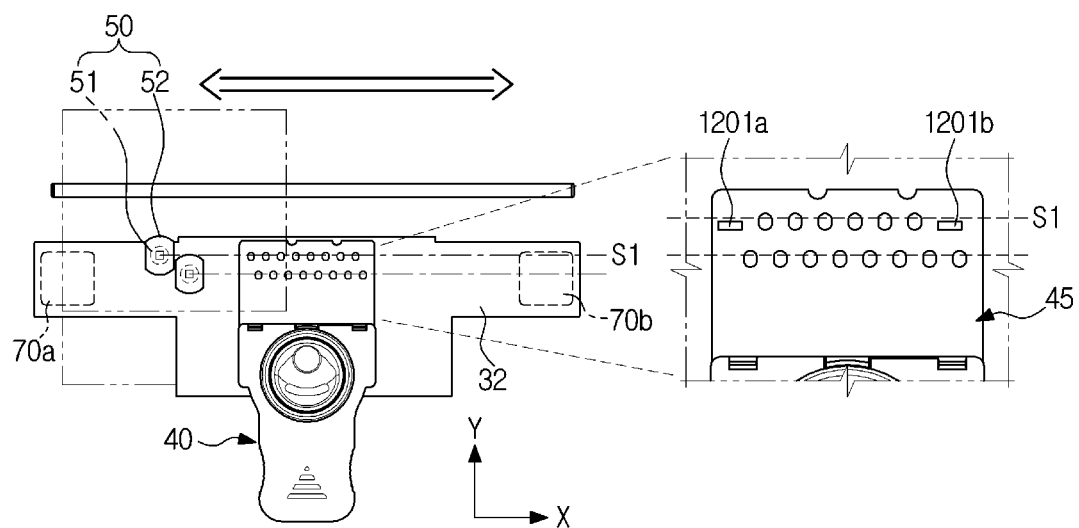
Figure 12B:
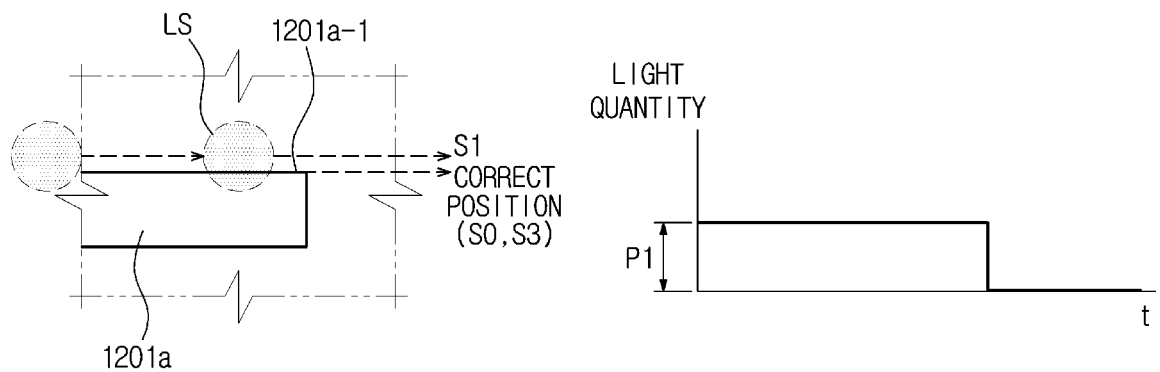

On the other hand, as illustrated in (a) of FIG. 12B, the fluid accommodating cartridge 40 may be abnormally mounted to the fluid analysis apparatus 1. In this case, as illustrated in (b) of FIG. 12B, a scan direction S1 of the measurement portion 50 may proceed such that the central portion of the beam spot LS deviates from the one surface 1201a-1 of the slit 1201a. In this case, the optical signal related to the slit 1201a measured by the measurement portion 50 may have a strength P1 as shown (c) of FIG. 12B.

The fluid analysis apparatus 1 identifies whether the fluid accommodating cartridge 40 is normally mounted in FIG. 12B based on the strength P0 of the optical signal obtained when the fluid accommodating cartridge 40 is normally mounted in FIG. 12A.

For example, when the fluid accommodating cartridge 40 is mounted abnormally, the strength P1 of the optical signal measured in FIG. 12B may have a value different from that of the strength P0 of the optical signal measured in FIG. 12A when the fluid accommodating cartridge 40 is normally mounted.

For example, the strength P1 of the optical signal measured in FIG. 12B may be smaller than the strength P0 of the optical signal shown in FIG. 12A. In addition, when using a plurality of slits 1201a and 1201b, an average value (or an average value of absolute values) for the strengths P1 of the optical signal measured by the plurality of slits 1201a and 1201b, a maximum value for the strengths P1 of the optical signal, or a sum value for the strengths P1 of the optical signal may be different from values for the strengths P0 of the optical signal measured when the fluid accommodating cartridge 40 is normally mounted as in FIG. 12A.

Accordingly, the fluid analysis apparatus 1 identifies that the fluid analysis cartridge 40 is abnormally mounted when the difference in the strength of the optical signal is outside a preset allowable range, and identifies that the fluid analysis cartridge 40 is normally mounted when the difference in the strength of the optical signal is within the preset allowable range.

On the other hand, in FIG. 12B, the fluid analysis apparatus 1 may identify whether the fluid accommodating cartridge 40 is abnormally mounted, but may have difficulty in identifying in which direction the fluid accommodating cartridge 40 is deviated.

Figure 12C:
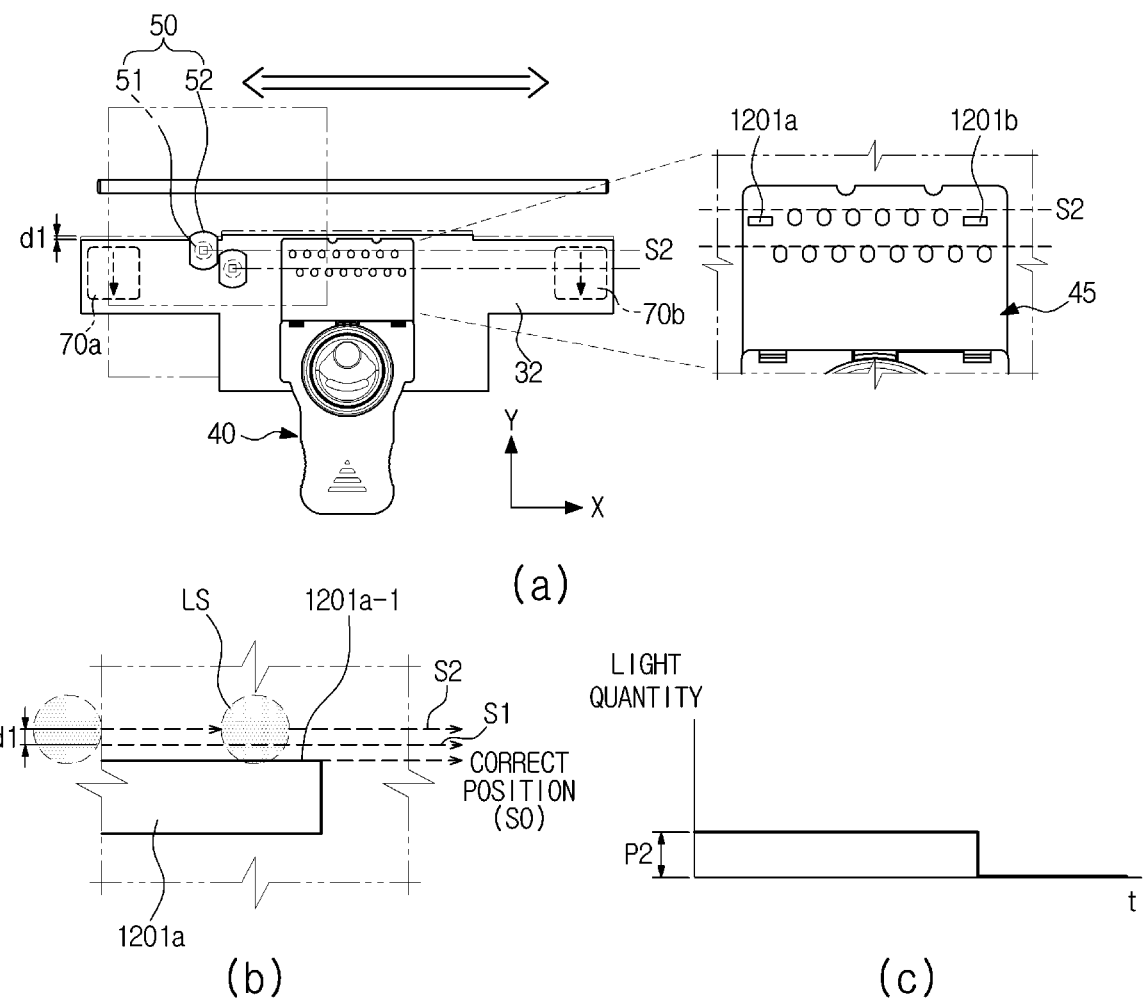

As illustrated in (a) of FIG. 12C, in order to identify the mis-installation direction of the fluid accommodating cartridge 40, the fluid analysis apparatus 1 controls the actuators 70a and 70b to move the mounting portion 32 by a predetermined distance d1 in a predetermined direction (the downward direction of the Y-axis). In this case, as illustrated in (b) of FIG. 12C, a rescan direction S2 of the measurement portion 50 may procced to have the center of the beam spot LS further deviated from the one surface 1201a-1 of the slit 1201a. In this case, the optical signal related to the slit 1201a measured by the measurement portion 50 may have a strength P2 as shown in (c) of FIG. 12C.

As a result of the rescan, the strength P2 of the optical signal measured in FIG. 12C may be less than the strength P1 of the optical signal measured in FIG. 12B. Accordingly, the fluid analysis apparatus 1 may determine that the fluid accommodating cartridge 40 is deviated in the downward direction of the y-axis in comparison to a case in which the fluid accommodating cartridge 40 is normally mounted.

On the other hand, as a result of the rescanning of the slit 1201a, when the strength P2 of the optical signal measured in FIG. 12C is measured is greater than the strength P1 of the optical signal measured in FIG. 11B, the fluid analysis apparatus 1 may determine that the fluid accommodating cartridge 40 is deviated in the upward direction of the y-axis in comparison to a case in which the fluid accommodating cartridge 40 is normally mounted.

When the mis-installation direction of the fluid accommodating cartridge 40 is identified, the fluid analysis apparatus 1 may control the operation of the actuators 70a and 70b such that the strength of the optical signal related to the slit 1201a is within the allowable range based on the mis-installation direction.

Figure 12D:
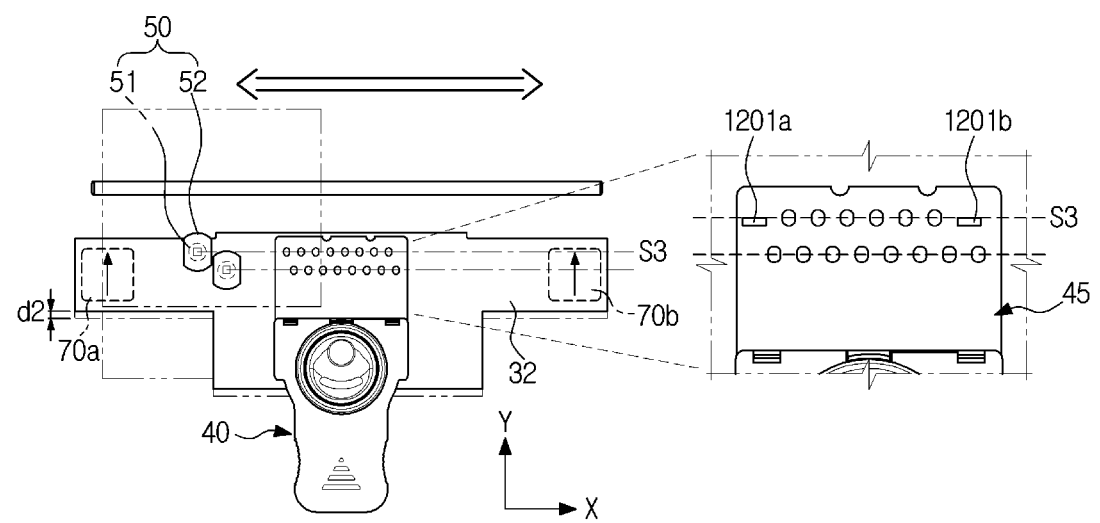
Figure 12D:
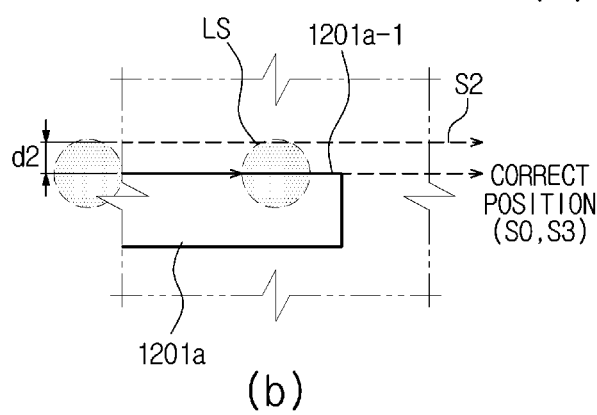
Figure 12D:
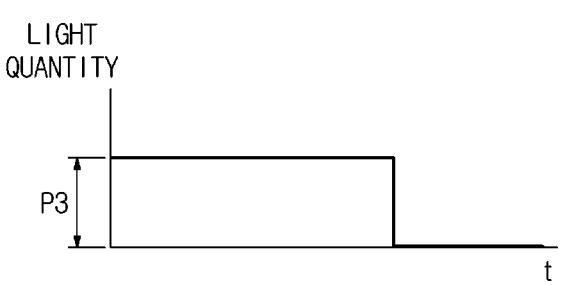

When it is identified that the fluid accommodating cartridge 40 is deviated in the upward direction in FIG. 12C, the fluid analysis apparatus 1 may move the fluid accommodating cartridge 40 in a predetermined direction (the downward direction of the Y-axis) by a predetermined distance d2 as shown in (a) of FIG. 12D. Then, in order to confirm that the fluid accommodating cartridge 40 is normally mounted, the fluid analysis apparatus 1 may rescan the slit 1201a of the fluid accommodating cartridge 40 as shown in (b) of FIG. 12D. When the fluid accommodating cartridge 40 is normally mounted, the rescan direction S3 of the measurement portion 50 may proceed such that the central portion of the beam spot passes through the one surface 1201a-1 of the slit 1201a. In this case, in FIG. 12D, the optical signal related to the slit 1201a measured by the measurement portion 50 may have a strength P3 that is equal or close to the strength P0 of the optical signal shown in FIG. 12A.

When it is identified that the strength P3 of the optical signal measured in FIG. 12D is within the allowable range in comparison to the strength P0 of the optical signal obtained when the fluid accommodating cartridge 40 is normally mounted in FIG. 12A, the fluid analysis apparatus 1 may determine that the fluid accommodating cartridge 40 is normally mounted. Accordingly, the fluid analysis apparatus 1 may end the alignment procedure and perform a subsequent procedure for inspecting and analyzing the fluid sample accommodated in the fluid accommodating device 1.

Figure 13:
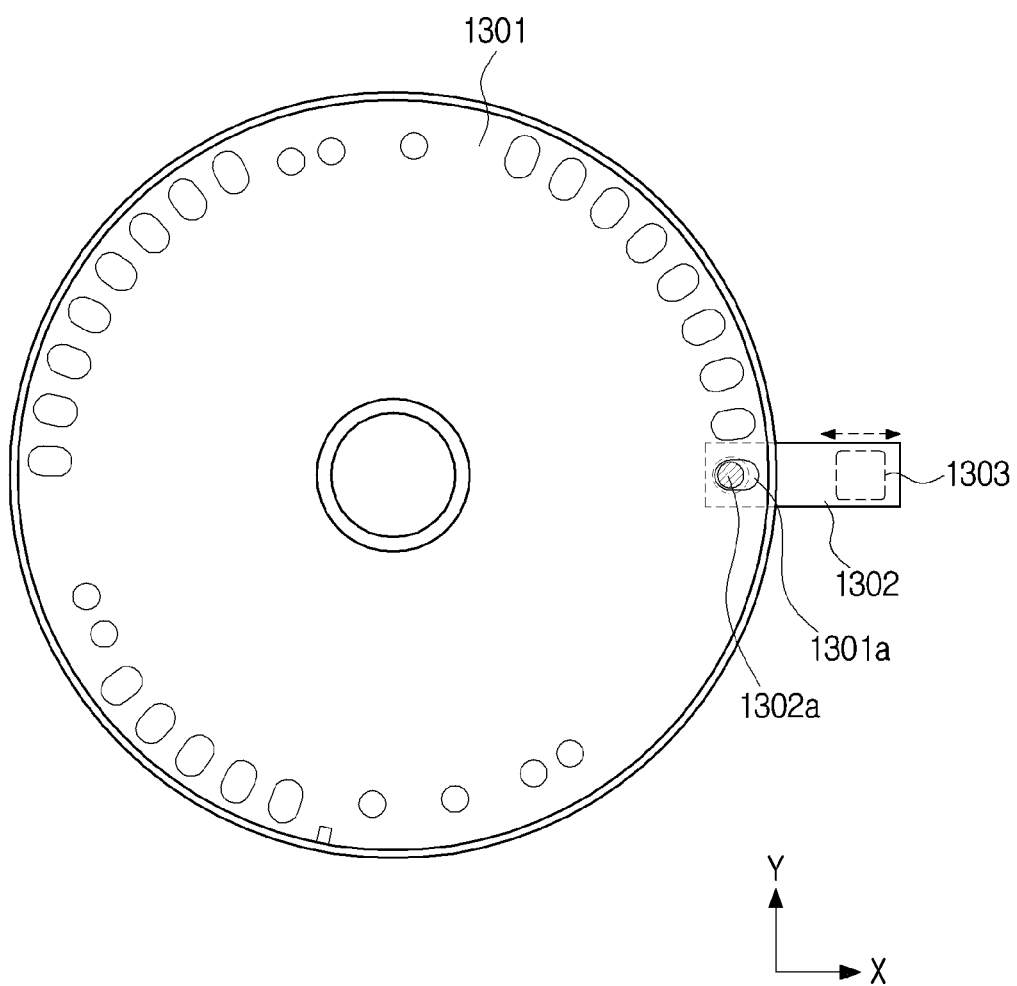
FIG. 13 is a view illustrating alignment performed on a disk-shaped fluid accommodating cartridge according to an embodiment of the disclosure.

FIG. 13 is a view illustrating alignment performed on a disk-shaped fluid accommodating cartridge according to an embodiment of the disclosure.

Referring to FIG. 13, a fluid accommodating cartridge 1301 may be designed in the form of a disc.

As the disk-shaped fluid accommodating cartridge 1301 is rotated, wells 1301a provided in the fluid accommodating cartridge 1301 may be sequentially scanned by a measurement portion 1302.

In this case, in order to align the well 1301a provided in the fluid accommodating cartridge 1301 with the measurement portion 1302, an actuator 1303 may be provided on at least one of the fluid accommodating cartridge 1301 or the measurement portion 1302. The actuator 1303 may align the well 1301a with the measurement portion 1302 by moving the fluid accommodating cartridge 1301 or the measurement portion 1302.

In an embodiment, referring to in FIG. 13, when the actuator 1303 is provided on the measurement portion 1302, the actuator 1303 may adjust the position of a beam spot 1302a transmitted to the well 1301a by moving the measurement portion 1302. In this case, the fluid accommodating cartridge 1301 may be rotated in one direction, so that the actuator 1303 even with a degree of freedom of driving in one axis (X-axis direction) may provide an effect of aligning the well 1301a and the measurement portion 1302 similar to driving of an actuator having a degree of freedom of driving in multi-axis directions.

Figure 14:
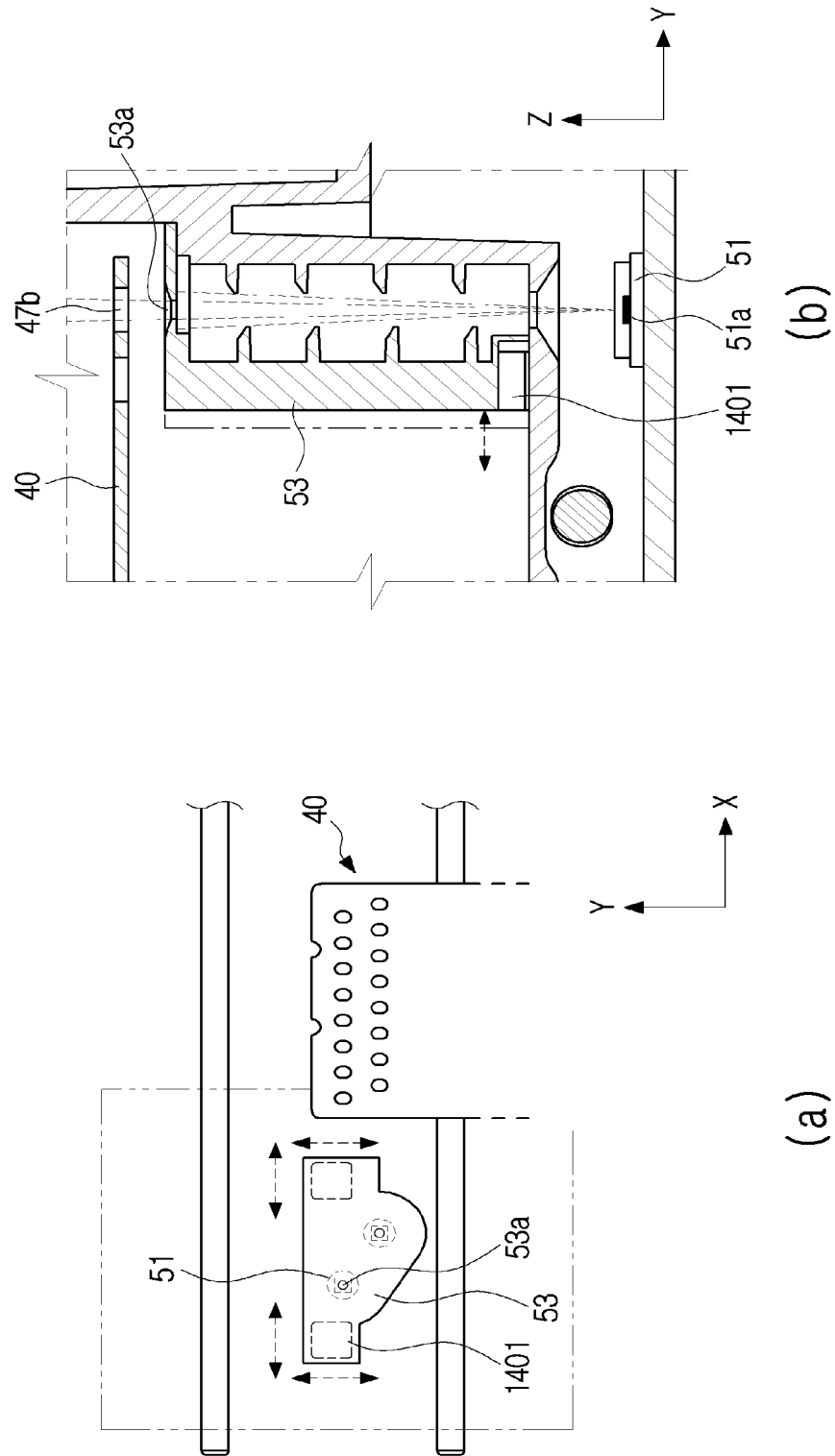
FIG. 14 is a view illustrating alignment performed by moving a pin hole according to an embodiment of the disclosure.

FIG. 14 is a view illustrating an operation of performing alignment by moving a pin hole according to an embodiment of the disclosure.

In (a) and (b) of FIG. 14, the fluid analysis apparatus 1 may align the well 47b with the measurement portion 50 by moving a pin hole portion 53 of the measurement portion 50. A pin hole 53a of the pin hole portion 53 may include an opening that transmits only a part of the light emitted from the light source 51a of the light source portion 51, focuses the light emitted from the light source 51a, or limits the light flux of the light emitted from the light source 51a. The pin hole 53a may cause a beam spot to be formed in the well 47b.

In (a) and (b) of FIG. 14, an actuator 1401 may be provided in the pin hole portion 53. The fluid analysis apparatus 1 transfers the pin hole portion 53 in one axis direction (Y-axis direction or X-axis direction) to align the well 47b and the measurement portion 50 with each other so that a beam spot is formed in the central portion of the well 47b. Alternatively, the fluid analysis apparatus 1 may transfer the pin hole portion 53 in multi-axis directions (Y-axis direction and X-axis direction) to align the well 47b and the measurement portion 50 with each other.

Figure 15:
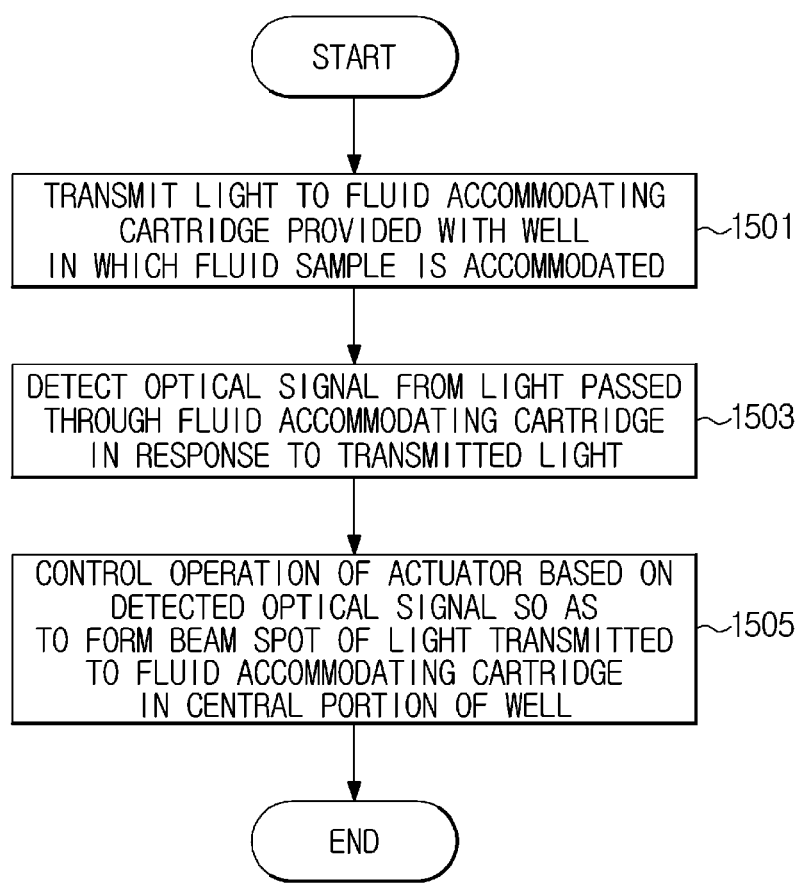
FIG. 15 is a flowchart showing a method of controlling a fluid analysis apparatus according to an embodiment of the disclosure.

FIG. 15 is a flowchart showing a method of controlling the fluid analysis apparatus 1 according to an embodiment of the disclosure.

In operation 1501, the fluid analysis apparatus 1 may transmit light to the fluid accommodating cartridge 40 provided with the well 47b in which a fluid sample is accommodated.

In operation 1503, the fluid analysis apparatus 1 may detect an optical signal from light passed through the fluid accommodating cartridge 40 in response to the transmitted light.

In operation 1505, in order to perform accurate inspection of the fluid sample, the fluid analysis apparatus 1 may control an operation of the actuator 70 based on the detected optical signal such that a beam spot of light transmitted to the fluid accommodating cartridge 40 is formed in the central portion of the well 47b.

For example, the fluid analysis apparatus 1 controls the operation of the actuator 70 to align the measurement portion 50 for transmitting light and the well 47b with each other such that the beam spot of light is formed at the central portion of the well 47b. In this case, the controlling of the operation of the actuator 70 such that the measurement portion 50 and the well 47b are aligned with each other may include controlling the operation of the actuator 70 such that the center of the light source portion 51 for transmitting light to the well 47b of the fluid accommodating cartridge, the center of the light detection portion 52 for detecting optical signals from the transmitted light, and the center of the well 47b are vertically in line with each other within an error range of a predetermined diameter.

In one embodiment, when controlling the operation of the actuator, the fluid analysis apparatus 1 may control the operation of the actuator 70 based on the width of the optical signal measured by the measurement portion 50. For example, when the width of the optical signal is outside an allowable range, the fluid analysis apparatus 1 may identify that the fluid accommodating cartridge 40 is abnormally mounted, and control the operation of the actuator 70 such that the width of the optical signal is within the allowable range.

In another embodiment, when controlling the operation of the actuator, the fluid analysis apparatus 1 may control the operation of the actuator 70 based on the strength of the optical signal measured by the measurement portion 50. For example, when the strength of the optical signal is outside an allowable range, the fluid analysis apparatus 1 may identify that the fluid accommodating cartridge 40 is abnormally mounted, and control the operation of the actuator 70 such that the strength of the optical signal is within the allowable range.

The various embodiments of the disclosure and terminology used herein are not intended to limit the technical features of the disclosure to the specific embodiments, but rather should be understood to cover all modifications, equivalents, and alternatives falling within the spirit and scope of the invention. In the description of the drawings, like numbers refer to like elements throughout the description of the drawings. The singular forms preceded by "a," "an," and "the" corresponding to an item are intended to include the plural forms as well unless the context clearly indicates otherwise. In the disclosure, a phrase such as "A or B," "at least one of A and B," "at least one of A or B," "A, B or C," "at least one of A, B and C," and "at least one of A, B, or C" may include any one of the items listed together in the corresponding phrase of the phrases, or any possible combination thereof. Terms, such as "first," "second," etc. are used to distinguish one element from another and do not modify the elements in other aspects (e.g., importance or sequence). When one (e.g., a first) element is referred to as being "coupled" or "connected" to another (e.g., a second) element with or without the term "functionally" or "communicatively," it means that the one element is connected to the other element directly, wirelessly, or via a third element.

The various embodiments of the present disclosure may be realized by software including one or more instructions stored in a machine-readable storage media (e.g., the memory 80,) that can be read by a machine (e.g., a computer). The machine refers to an apparatus that may invoke and execute the instruction stored in the storage medium and operate in accordance with the invoked instruction, and the machine may include the fluid analysis apparatus 1 according to the disclosed embodiments. When the command is executed by a processor (e.g., the controller 90), the processor may perform a function corresponding to the instruction directly or by using other components under the control of the processor. The instruction may include codes generated by a compiler or codes executable by an interpreter. The machine-readable storage medium may be provided in the form of a non-transitory storage medium. Here, when a storage medium is referred to as "non-transitory," it can be understood that the storage medium is tangible and does not include a signal, but rather that data is semi-permanently or temporarily stored in the storage medium.

According to one embodiment, the methods according to the various embodiments disclosed herein may be provided in a computer program product. The computer program product may be traded between a seller and a buyer as a product. The computer program product may be distributed in the form of a machine-readable storage medium (e.g., compact disc read only memory (CD-ROM)), or may be distributed through an application store (e.g., Play Store™) online. In the case of online distribution, at least a portion of the computer program product may be stored at least semi-permanently or may be temporarily generated in a storage medium, such as a memory of a server of a manufacturer, a server of an application store, or a relay server.

According to the various embodiments, each of the above-described elements (e.g., a module or a program) may include a singular or plural entity, or some of sub-elements may be omitted, or other sub-elements may be added. Alternatively or additionally, a plurality of elements (e.g., modules or programs) may be integrated into one element. In this case, the integrated element may perform one or more functions of each of the plurality of elements in the same or similar manner as that performed by the corresponding element of the plurality of components before the integration. According to various embodiments, operations performed by a module, program, or other elements may be executed sequentially, in parallel, repeatedly, or heuristically, or one or more of the operations may be executed in a different order, or omitted, or one or more other operations may be added.

The invention claimed is:

1. A fluid analysis apparatus comprising:
  an actuator provided on a part of the fluid analysis apparatus;
  a mounting portion on which a fluid accommodating cartridge is mounted thereon, the fluid accommodating cartridge provided with a well in which a fluid sample is accommodated;
  a measurement portion configured to transmit light to the fluid accommodating cartridge and detect an optical signal from the light passed through the fluid accommodating cartridge, the measurement portion comprising:
- a light source configured to transmit light to the well of the fluid accommodating cartridge; and
- a light detector configured to detect optical signals from the transmitted light; and a controller comprising at least one processor, the controller being configured to control an operation of the actuator to move at least a portion of the measurement portion or the mounting portion based on a width of a strength value of the optical signal detected by the measurement portion, to cause the light transmitted from the measurement portion to pass through a central portion of the well to perform an accurate inspection on the fluid sample, wherein the width corresponds to a length of time in which the strength value is detected by the measurement portion.

2. The fluid analysis apparatus of claim 1, wherein the controller is further configured to control the operation of the actuator to align the measurement portion with the well to cause the light transmitted from the measurement portion to pass through the central portion of the well.

3. The fluid analysis apparatus of claim 2,
wherein the controller is further configured to control the operation of the actuator to move at least the portion of the measurement portion or the mounting portion to cause a center of the light source, a center of the light detector, and a center of the well to be vertically in line with each other within an error range of a predetermined diameter.

4. The fluid analysis apparatus of claim 1, wherein the actuator is provided on the mounting portion or the measurement portion, and
the controller is further configured to control the operation of the actuator to move at least the portion of the mounting portion or the measurement portion to cause the light transmitted from the measurement portion to pass through the central portion of the well.

5. The fluid analysis apparatus of claim 4, wherein the controller is further configured to control the operation of the actuator to move a pin hole portion included in the measurement portion.

6. The fluid analysis apparatus of claim 1, wherein the controller is further configured to:
identify that the fluid accommodating cartridge is abnormally mounted based on the width of the strength value of the optical signal being outside of an allowable range, and
control the operation of the actuator to cause the width of the strength value of the optical signal to be within the allowable range.

7. The fluid analysis apparatus of claim 6, wherein the controller is further configured to:
upon identifying that the fluid accommodating cartridge is abnormally mounted, identify a mis-installation direction of the fluid accommodating cartridge based on a change in the width of the strength value while controlling the operation of the actuator, and
control, based on the mis-installation direction that is identified, the operation of the actuator to cause the width of the strength value of the optical signal to be within the allowable range.

8. The fluid analysis apparatus of claim 1, wherein the measurement portion is further configured to transmit the light to at least one of the well or a groove provided in the fluid accommodating cartridge, and detect the optical signal from the light passed through the at least one of the well or the groove.

9. The fluid analysis apparatus of claim 1, wherein the fluid analysis apparatus further comprises a plurality of actuators, including the actuator, that are mounted on the mounting portion, and the controller is further configured to control the plurality of actuators to move the mounting portion in an upward direction, a downward direction, a clockwise direction, or a counter-clockwise direction.

10. A fluid analysis apparatus comprising:
an actuator provided on a part of the fluid analysis apparatus;
a mounting portion on which a fluid accommodating cartridge is mounted thereon, the fluid accommodating cartridge provided with a well in which a fluid sample is accommodated;
a measurement portion configured to transmit light to the fluid accommodating cartridge and detect an optical signal from the light passed through the fluid accommodating cartridge, the measurement portion comprising:
- a light source configured to transmit light to the well of the fluid accommodating cartridge; and
- a light detector configured to detect optical signals from the transmitted light; and a controller comprising at least one processor, the controller being configured to control an operation of the actuator to move at least a portion of the measurement portion or the mounting portion based on a strength of the optical signal detected by the measurement portion, to cause the light transmitted from the measurement portion to pass through a central portion of the well to perform an accurate inspection on the fluid sample, wherein the controller is further configured to:
identify that the fluid accommodating cartridge is abnormally mounted based on the strength of the optical signal being outside of an allowable range,
upon identifying that the fluid accommodating cartridge is abnormally mounted, identify a mis-installation direction of the fluid accommodating cartridge based on a change in the strength of the optical signal while controlling the operation of the actuator, and
control, based on the mis-installation direction that is identified, the operation of the actuator to cause the strength of the optical signal to be within the allowable range.

* * * * *